United States Patent [19]
Russell et al.

[11] Patent Number: 6,156,303
[45] Date of Patent: Dec. 5, 2000

[54] ADENO-ASSOCIATED VIRUS (AAV) ISOLATES AND AAV VECTORS DERIVED THEREFROM

[75] Inventors: David W. Russell; Elizabeth A. Rutledge, both of Seattle, Wash.

[73] Assignee: University of Washington, Seattle, Wash.

[21] Appl. No.: 08/873,168

[22] Filed: Jun. 11, 1997

[51] Int. Cl.$^7$ .......................... A61K 48/00; C12N 15/864; C12N 15/64; C12N 5/10

[52] U.S. Cl. ..................... 424/93.2; 424/93.6; 435/69.1; 435/320.1; 435/455; 435/456; 435/457; 435/462; 435/463; 435/325; 435/366; 435/371; 536/23.72; 536/24.3

[58] Field of Search .................. 435/69.1, 320.1, 435/455, 456, 457, 462, 463, 325, 366, 371; 536/23.1, 23.72, 24.3; 424/93.2, 93.6

[56] References Cited

U.S. PATENT DOCUMENTS

| | | | |
|---|---|---|---|
| 5,252,479 | 10/1993 | Srivastava | 435/235.1 |
| 5,587,308 | 12/1996 | Carter | 435/371 |
| 5,858,351 | 1/1999 | Podsakoff et al. | 424/93.2 |

OTHER PUBLICATIONS

Muramatsu et al., "Nucleotide Sequencing and Generation of an Infectious Clone of Adeno–Associated Virus 3," *Virology* 221:208–217 (1996).

Srivastava et al., "Nucleotide Sequence and Organization of the Adeno–Associated Virus 2 Genome," *J. Virol.* 45:555–564 (1983).

Alexander et al., "Effects of Gamma Irradiation on the Transduction of Dividing and Nondividing Cells in Brain and Muscle of Rats by Adeno–Associated Virus Vectors," *Human Gene Ther.* 7:841–850 (1996).

Flotte et al., "Stable in vivo Expression of the Cystic Fibrosis Transmembrane Conductance Regulator with an Adeno–Associated Virus Vector," *Proc. Natl. Acad. Sci., USA* 90:10613–10617 (1993).

Russell et al., "Adeno–Associated Virus Vectors Preferentially Transduce Cells in S Phase," *Proc. Natl. Acad. Sci., USA* 91:8915–8919 (1994).

Halbert et al., "Adeno–Associated Virus Vectors Transduce Primary Cells Much Less Efficiently than Immortalized Cells," *J. Virol.* 69:1473–1479 (1995).

Mizukami et al., "Adeno–Associated Virus Type 2 Binds to a 150–Kilodalton Cell Membrane Glycoprotein," *Virology* 217:124–130 (1996).

Clark et al., "Cell Lines for the Production of Recombinant Adeno–Associated Virus," *Hum. Gene Ther.* 6:1329–1341 (1995).

*Primary Examiner*—David Guzo
*Attorney, Agent, or Firm*—Cambell & Flores LLP

[57] ABSTRACT

The present invention provides isolated adenovirus-associated viruses ("AAV"), including AAV isolates designated AAV3B and AAV6. The invention also provides nucleic acid molecules of AAV3B (SEQ ID NO: 1) or AAV6 (SEQ ID NO: 2), including DNA or RNA, and provides substantially purified polypeptides encoded by AAV3B or AAV6, as well as antibodies specific for such polypeptides. The invention also provides infectious AAV3B and AAV6 clones; AAV viral vectors, which can be hybrid AAV viral vectors; AAV vector plasmids; and AAV helper plasmids; each comprising at least a portion of an AAV3B (SEQ ID NO: 1) or AAV6 (SEQ ID NO: 2) nucleic acid molecule. The invention further provides host cells containing at least a portion of an AAV3B or AAV6 nucleic acid molecule and progeny cells derived therefrom, and provides non-human transgenic mammals having an AAV vector genome stably integrated in a chromosome. The invention also provides methods of producing a polypeptide or an RNA by expressing the polypeptide or the RNA from an AAV viral vector in a cell, and methods of treating a pathologic condition in a mammal, comprising transducing cells of the mammal with an AAV viral vector containing a heterologous nucleic acid sequence. The invention also provides AAV3B or AAV6 nucleotide sequences, which can be useful, for example, as probes for identifying the presence of AAV3B or AAV6 nucleic acids in a sample. The present invention further provides a method of identifying an AAV viral vector suitable for administration to an individual.

32 Claims, 13 Drawing Sheets

| | | | | | | | |
|---|---|---|---|---|---|---|---|
| AAV6 | 3294 | CTCCCtCCGT | CTGTTTCATG | aTcCGgCAGT | ACGGcTACCT | aACgCTcAAC | AAtGGcAGcC | AGGCAGTGGG | ACGgTCATCC | TTTTACTGCC | 3393 |
| AAV3B | 3291 | CTCCCGCCGT | CGTCTTCATG | GTCCCTCAGT | ATGGATACCT | CACCCTGAAC | AAcGgGAGTC | AaGCggTGGG | ACGCTCATCC | TTTTACTGCC | 3390 |
| AAV2 | 3286 | CTCCCGCCGT | CGTCTTCATG | GTgCCaCAGT | ATGGATACCT | CACCCTGAAC | AACGGgAGTC | AGGCAGTaGG | ACGCTCtTCa | TTTTACTGCC | 3385 |
| AAV6 | 3394 | TGGAaTATaTT | CCCaTCGCAG | ATGCTGAGaA | CgGGcAATAA | CTTTACCTTC | AGCTACACCT | TCGAGGACGT | gCCTTTCCAC | AGCAGCTACG | CgCACAGCCA | 3493 |
| AAV3B | 3391 | TGGAGTACTT | CCCTTCGCAG | ATGCTaAGgA | CTGGAAATAA | CTTCcaaTTC | AGCTATACCT | TCGAGGATgT | aCCTTTTCAC | AGCAGCTACG | CTCACAGCCA | 3490 |
| AAV2 | 3386 | TGGAGTACTT | tCCTTCtCAG | ATGCTGcCTA | CCGGAAAACA | CTTTACCTTC | AGCTACACTt | TtGAGGACGT | tCCTTTCCAC | AGCAGCTACG | CTCACAGCCA | 3485 |
| AAV6 | 3494 | GAGcCTGGAC | CGgCTGATGA | ATCCTCTCAT | CGACCAGTAC | CTGTATTACC | TGAACAGAAC | tCAgAaTCag | gTgCCcAACA | caaggactTG | 3590 |
| AAV3B | 3491 | GAGTTGGAT | CGCTtGATGA | ATCCCTCTtAT | tGATCAGTAT | CTGTACTACC | TGAACAGAAC | gCAaggaaCA | CaACCAACCA | aTCACGGCTG | 3590 |
| AAV2 | 3486 | GAGTCTGGAC | CGtCTCATGA | ATCCTCTCAT | CGACCAGTAC | CTGTATTACT | TGAgCAGAAC | aaaCACTCCA | Ag---TGGAA | gTCAaGGCTt | 3582 |
| AAV6 | 3591 | CTGTTTAGCC | gGGggtCtCC | agcTGgCATG | TCTGTTaGc | CCAaAAACTG | GCTACCTGGA | CCCTGTTACC | CGTTTCTAAa | ACAaaaACaG | 3690 |
| AAV3B | 3591 | CTTTTTAGCC | AGGCTGGGCC | tCagtCtATG | TCTtTgCAGg | CCAGAAATTG | GCTACCTGGG | CCCTGCTACC | ACTTTCAAAG | ACTgCTAacg | 3690 |
| AAV2 | 3583 | CaGTTTtctC | AGGCCGGaGC | gagTGaCATt | cggGaCCAGt | CTaGGgAACTG | GCTtCCTGGA | CCCTGTTACC | AGTaTCAAAG | ACATCTgCgG | 3682 |
| AAV6 | 3691 | ACAACAACAA | CAGCAACTTT | aCCTGGACTG | GtGCTTCaAA | AaTCTgCTGG | AAtGGGgCTG | cAAcCCTgGC | aCTgCTATGG | CCTcaCACAA | 3790 |
| AAV3B | 3691 | ACAACAACAA | CAGTAACTTT | CCTTGGACaG | cgGCcAGcAg | ATATaAACCAA | AATGGCCGcG | ACCG | CCAgTCCaGGa | CCAGTCACAA | 3790 |
| AAV2 | 3683 | AtAACAACAA | CAGTGaATac | tCgTGGACTG | GaGCTACCAA | gTAcCACCTC | AATGGCaGAG | ACTCTCTGGT | CCgGCCATGG | CaAGcCACAA | 3782 |
| AAV6 | 3791 | aGACGAcAaA | GACAAGTTCT | TTCCCATGAG | CGgtGTcatg | ATtTTTGGaA | AGGAgaGCgC | cGgaGCttcA | TgGACAATGT | CATGATCACA | 3890 |
| AAV3B | 3791 | GGACGATGAA | GAAAATGAA | TCCCTCATgca | CGGcaaTCTa | ATaTTTGGCA | AaGAAGGGaC | AacGGCAAgt | TaGAtAATGT | aATGATTACg | 3890 |
| AAV2 | 3783 | GGACGATGAA | GAAAAGTTTT | TTCCTCAgAG | CGGGGTTCTC | ATCTTTGGGA | AGCAAGGGCtC | AGaGaaAACA | AATGtGGAca | TtGAaAAggT | CATGATTACA | 3882 |

FIG. 1F

```
AAV6   3891 GACGAAGAGG AAATCAaagC CACtAaCCCC GTGGCCACCG AaagaTtTGG gACTGTGGCA gtCAAtCTCC AGAGCaGCAg CACAGAcCCt GCGACCGGAG 3990
AAV3B  3891 GATGAAGAaG AgATTcGTAC CACCAATCCt GTGGCaACaG AGCAGTATGG aACTGTGGCA AataACTtGc tACAGctCCc aCGACtaGAa 3990
AAV2   3883 GACGAAGAGG AAATCAGGaC aACCAATCCC GTGGCtACgg AGCAGTATGG ttCtGTatCt ACCAACCTCC AGAGaGCAA CAGAcAagCa GCtACCgCAG 3982

AAV6   3991 ATGTgCATGt TatGGGaGCC TTACCTGGaA TGGTGTGGCA AGACAGAGAC GTaTACCTgC AGGGtCCTAT tTGGGCCAAAg ATTCCTCACA CGGATGGACA 4090
AAV3B  3991 CTGTCAATGa GATTCAGTGa TTACCTGGCC TGGTGTGGCA AGAtCGtGAC GTGTACCTTC AaGGaCCTAT CTGGGCAAAG ATTCCTCACA CGGATGGACA 4090
AAV2   3983 ATGTCAAcac aCAaGGCGtt cTtCCaGGCA TGGTCTGGCA gGACAGAGAt GTGTACCTTC AGGGgCCCAT CTGGGCAAAG ATTCCaCACA CGGAcGGACA 4082

AAV6   4091 CTTTTCACCCg TCTCCCTCTCA TGGGCGGCTT TGGACTTAAg CACCCGCCTC CTCAGATCCT CATCAAAAAAC ACgCCTgTTC CTGCGAATCC AGCAAAACGCT 4190
AAV3B  4091 CTTTTCAtCCt TCTCCCTCtgA TGGGaGGCTT TGGACTgGaCT CATCCGGACA CTCAaATCaT gATCAAAAAt ACtCCGGTAC CgGCaAATCC AGCAAAACGCT 4190
AAV2   4083 tTTTCACCCC TCTCCCCTCA TGGGtGGaTT CGGACTTAAA CACCCGCCTC CaCAGATTCT CaTCAAGaAC ACCCGGTAC CTGCGAATCC TtGCACCACc AGCAAAACGCT 4182

AAV6   4191 TTttcgGCTa CAAAGTTTGC TTCATTCATC ACcCAGTACT CCACaGGACA aGTgAGCGTG GGGAGCTGCA GAAAGAAAAC AGCAAAACGCT 4290
AAV3B  4191 TTCAGcCCGG CCAAGTTTGC TTCATTtATC ACtCAGTACT CCACtGGACA GGTCAGCGTG GGGAGCTGCA GAAAGGAAAAC AGCAAAACGCT 4290
AAV2   4183 TTCAGtGCGG CAAAGTTTGC TTCcTTCATC ACaCAGTACT CCACggGACA GGTCAGCGTG GGGAGCTGCA GAAAGGAAAAC AGCAAAACGCT 4282

AAV6   4291 GGAATCCCGA AgTgCAGTGA AtgcaAaAtC TGCcAACGTt GAtTTCACTG TGGACAAcAA TGGaCTTTAT ACTGAGCCT GCCCCATTGG GCCCCATTGG 4390
AAV3B  4291 GGAATCCaGA gATTCAGtGA ACaTCcCAACT ACAACAAGTC TGTTAATGTG GACTTTACTG TaGACACTAA TGGtGTTTAT AgTGAaCTTC GCCCtATTGG 4390
AAV2   4283 GGAATCCCGA AATTCAGTAC ACAACAAGTC TGTTAATGTG GACTTTACTG TGGACACTAA TGGCGTGTAT tCaGAGCCTC GCCCCATTGG 4382
                                                                                         poly A signal      RNA termini AAV6   4391 CACCCGtTAC CTCACCCGTc CCCTGTAATT GTGTGTTAAT CAATAAACCG CTTTGG-TCT gTCAGTTGAA TTATCTTATC 4489
AAV3B  4391 aACCCGgTAT CTCACaCGgA ACTtGTAATc CTG-GTTAAT CAATAAACCG TTCAGTTGAA TTCAGTTGAA TTATCTTATC 4489
AAV2   4383 CACCaGaTAC CTgACTCGTA AtCTGTAATT GCtTGTTAAT CAATAAACCG TTTAATTCGT TTCAGTTGAA CTTTCTTATC 4481
```

FIG. 1G

```
AAV6   1    MAADGYLPDW  LEDNLSEGIR  EWWDLKPGAP  KPKANQQKQD  DGRGLVLPGY  KYLGPENGLD  KGEPVNAADA  AALEHDKAYD   80
AAV3B  1    MAADGYLPDW  LEDNLSEGIR  EWWALKPGVP  QPKANQQHQD  NRRGLVLPGY  KYLGPGPNGLD KGEPVNEADA  AALEHDKAYD   80
AAV3A  1    MAADGYLPDW  LEDNLSEGIR  EWWALKPGVP  QPKANQQHQD  NRRGLVLPGY  KYLGPGNGLD  KGEPVNEADA  AALEHDKAYD   80
AAV2   1    MAADGYLPDW  LEDILSEGIR  QWWKLKPGPP  PKPAERHKD   DSRGLVLPGY  KYLGPFNGLD  KGEPVNEADA  AALEHDKAYD   80
                                                                                      ┌─ VP2

AAV6   81   QQLKAGDNPY  LRYNHADAEF  QERLQEDTSF  GGNLGRAVFQ  AKKRVLEPEG  LVEEGAKTAP  GKKRPVEQSP  QEPDSSSGTG  160
AAV3B  81   QQLKAGDNPY  LKYNHADAEF  QERLQEDTSF  GGNLGRAVFQ  AKKRILEPLG  LVEEAAKTAP  GKKRPVDQSP  QEPDSSSGVG  160
AAV3A  81   QQLKAGDNPY  LKYNHADAEF  QERLQEDTSF  GGNLGRAVFQ  AKKRILEPLG  LVEEAAKTAP  GKKRGAVDQSP QEPDSSSGVG  160
AAV2   81   RQLDSGDNPY  LKYNHADAEF  QERLKEDTSF  GGNLGRAVFQ  AKKRVLEPLG  LVEEPVKTAP  GKKRPVEHSP  VEPDSSSGTG  160
                                                                                 ┌─ VP3

AAV6   161  KTGQQPAKKR  LNFGQTGDSE  SVPDPQPLGE  PPATPAAVGP  TTMASGGGAP  MADNNEGADG  VGNASGNWHC  DSTWLGDRVI  240
AAV3B  161  KSGKQPARKR  LNFGQTGDSE  SVPDPQPLGE  PPAAPTSLGS  NTMASGGGAP  MADNNEGADG  VGNSSGNWHC  DSQWLGDRVI  240
AAV3A  161  KSGKQPARKR  LNFGQTGDSE  SVPDPQPLGE  PPAAPTSLGS  NTMALGSGAP  MADNNEGADG  VGNSSGNWHC  DSQWLGDRVI  240
AAV2   161  KAGQQPARKR  LNFGQTGDAD  SVPDPQPLGQ  PPAAPSGLGT  NTMATGSGAP  MADNNEGADG  VGNSSGNWHC  DSTWLGDRVI  240

AAV6   241  TTSTRTWALP  TYNNHLYKQI  SSQSGASND   NHYFGYSTPW  GYFDFNRFHC  HFSPRDWQRL  INNNWGFRPK  RLNFKLFNIQ  320
AAV3B  241  TTSTRTWALP  TYNNHLYKQI  SSQS-GASND  NHYFGYSTPW  GYFDFNRFHC  HFSPRDWQRL  INNNWGFRPK  KLSFKLFNIQ  319
AAV3A  241  TTSTRTWALP  TYNNHLYKQI  SSQS-GASND  NHYFGYSTPW  GYFDFNRFHC  HFSPRDWQRL  INNNWGFRPK  KLSFKLFNIQ  319
AAV2   241  TTSTRTWALP  TYNNHLYKQI  SSQS-GASND  NHYFGYSTPW  GYFDFNRFHC  HFSPRDWQRL  INNNWGFRPK  RLNFKLFNIQ  319

AAV6   321  VKEVTTNDGV  TTIANNLTST  VQVFTDSEYQ  LPYVLGSAHQ  GCLPPFPADV  FMVPQYGYLT  LNNGSQAVGR  SSFYCLEYFP  400
AAV3B  320  VKEVTQNDGT  TTIANNLIST  VQVFTDSEYQ  LPYVLGSAHQ  GCLPPFPADV  FMIPQYGYLT  LNNGSQAVGR  SSFYCLEYFP  399
AAV3A  320  VRGVTQNDGT  TTIANNLTST  VQVFTDSEYQ  LPYVLGSAHQ  GCLPPFPADV  FMVPQYGYLT  LNNGSQAVGR  SSFYCLEYFP  399
AAV2   320  VKEVTQNDGT  TTIANNLTST  VQVFTDSEYQ  LPYVLGSAHQ  GCLPPFPADV  FMVPQYGYLT  LNNGSQAVGR  SSFYCLEYFP  399
```

FIG. 2A

```
AAV6   401 SQMLRTGNNF TFSYTFEDVP FHSSYAHSQS LDRLMNPLID QYLYYLNRTQ NQ-SGSAQNK DLLFSRGSPA GMSVQPKNWL 479
AAV3B  400 SQMLRTGNNF QFSYTFEDVP FHSSYAHSQS LDRLMNPLID QYLYYLNRTQ GTTSGTTNQS RLLFSQAGPQ SMSLQARNWL 479
AAV3A  400 SQMLRTGNNF QFSYTFEDVP FHSSYAHSQS LDRLMNPLID QYLYYLNRTQ GTTSGTTNQS RLLFSQAGPQ SMSLQARNWL 479
AAV2   400 SQMLRTGNNF TFSYTFEDVP FHSSYAHSQS LDRLMNPLID QYLYYLSRTQ NTPSGTTTGS RLQFSQAGAS DIRDQSRNWL 478

AAV6   480 PGPCYRQQRV SKTKTDNNNS NFTWTGASKY NLNGRESLIN PGTAMASHKD DKDKFFPMSG VMIFGKESAG ASNTALDNVM 559
AAV3B  480 PGPCYRQQRL SKTANDNNNS NFPWTAASKY HLNGRDSLVN PGPAMASHKD DEEKFFPMHG NLIFGKEGTT ASNAELDNVM 559
AAV3A  480 PGPCYRQQRL SKTANDNNNS NFPWTAASKY HLNGRDSLVN PGPAMASHKD DEEKFFPMHG NLIFGKEGTT ASNAELDNVM 559
AAV2   479 PGPCYRQQRV SKTSADNNNS EYSWTGATKY HLNGRDSLVN PGPAMASHKD DEEKFFPQSG VLIFGKQGSE KTNVDIEKVM 558

AAV6   560 ITDEEEIKAT NPVATERFGT VAVNLQSSST DPATGDVHVM GALPGMVWQD RDVYLQGPIW AKIPHTDGHF HPSPLMGGFG 639
AAV3B  560 ITDEEEIRTT NPVATEQYGT VANNLQSSNT APTTRTVNDQ GALPGMVWQD RDVYLQGPIW AKIPHTDGHF HPSPLMGGFG 639
AAV3A  560 ITDEEEIRTT NPVATEQYGT VANNLQSSNT APTTRTVNDQ GALPGMVWQD RDVYLQGPIW AKIPHTDGHF HPSPLMGGFG 639
AAV2   559 ITDEEEIRTT NPVATEQYGS VSTNLQRGNR QAATADVNTQ GVLPGMVWQD RDVYLQGPIW AKIPHTDGHF HPSPLMGGFG 638

AAV6   640 LKHPPPQILI KNTPVPANPP AEFSATKFAS FITQYSTGQV SVEIEWELQK ENSKRWNPEV QYTSNYAKSV NVDFTVDTNG 719
AAV3B  640 LKHPPPQIMI KNTPVPANPP TTFSPAKFAS FITQYSTGQV SVEIEWELQK ENSKRWNPEI QYTSNYNKSV NVDFTVDTNG 719
AAV3A  640 LKHPPPQIMI KNTPVPANPP TTFSPAKFAS FITQYSTGQV SVEIEWELQK ENSKRWNPEI QYTSNYNKSV NVDFTVDTNG 719
AAV2   639 LKHPPPQILI KNTPVPANPS TTFSAAKFAS FITQYSTGQV SVEIEWELQK ENSKRWNPEI QYTSNYNKSV NVDFTVDTNG 718

AAV6   720 LYTEPRPIGT RYLTRPL                                                                    736
AAV3B  720 VYSEPRPIGT RYLTRNL                                                                    736
AAV3A  720 VYSEPRPIGT RYLTRNL                                                                    736
AAV2   719 VYSEPRPIGT RYLTRNL                                                                    735
```

ADENO-ASSOCIATED VIRUS (AAV) ISOLATES AND AAV VECTORS DERIVED THEREFROM

This invention was made with government support under grant number PO1 HL53750 awarded by the National Institutes of Health. The government has certain rights in the invention.

BACKGROUND OF THE INVENTION

1. Field of the Invention

The present invention relates generally to adeno-associated viruses (AAV) and more specifically to AAV vectors and plasmids and uses thereof.

2. Background Information

Gene therapy holds great promise for treating various diseases, including cancer, atherosclerosis, cystic fibrosis and diabetes. In particular, gene therapy can provide a means to treat diseases that are caused due to a gene mutation, since a corresponding functional normal gene can be introduced into the cells containing the mutant gene, thereby allowing expression of a functional gene product.

Although numerous methods for introducing a gene into a mammalian subject have been examined, the use of viral vectors has generated the greatest interest. Depending on the particular virus, viral vectors provide several advantages, including, for example, host specificity, cell type specificity and stable integration of the vector containing the gene into the host cell chromosome. However, while a particular viral vector has certain advantages over others, each viral vector has certain limitations.

Viral vectors based on retroviruses have been examined most extensively. Retroviral vectors allow for integration of a heterologous gene into a host cell genome, which allows for the gene to be passed to daughter cells following cell division. However, retroviral vectors have a limited host range and only integrate into dividing cells, thus rendering them of little use for introducing a gene into terminally differentiated cells.

The use of adenovirus vectors avoids some of the problems that occur using retroviruses. In particular, adenoviruses exhibit a relatively limited tissue specificity and they can infect cells that are not dividing. However, adenovirus vectors do not integrate into the host cell genome and, therefore, the use of such vectors can result in the requirement that the gene therapy procedure be repeated numerous times. Unfortunately, adenoviruses are highly immunogenic and induce the expression of neutralizing antibodies, which prevent subsequent infection by the virus. Thus, the number of times an adenovirus vector effectively can be administered to a patient is limited.

Adeno-associated viruses (AAV) also have been used to construct viral vectors useful for gene therapy. AAV infect various mammalian cells with relatively high efficiency and, in the appropriate host and in the absence of helper virus, can integrate into the host cell genome. Furthermore, unlike retroviruses, which are associated with cancer, and adenoviruses, which are associated with respiratory pathologies, AAV does not appear to cause any human disease.

Various types of AAV have been described, including the most well studied member of the group, designated AAV2, and viral vectors based on AAV2 have been constructed. Although AAV2 vectors avoid some of the problems associated with other viral vectors, certain problems remain. For example, while AAV2 can efficiently infect some cell types, other cell types are infected at a much lower frequency or are refractory to infection. In addition, like adenovirus vectors, antibodies can be generated against AAV vectors. In fact, as many as 85% of the normal human population appear to have antibodies against various AAV types, particularly against AAV2.

The development of AAV vectors that can transduce cell types that otherwise are transduced with low efficiency would greatly increase the usefulness of AAV viral vectors. In addition, AAV vectors constructed from an AAV serotype to which a patient to be treated has not been exposed and, therefore, has not generated an immune response, will greatly increase the number of patients that can be treated using AAV vectors. Thus, a need exists to identify novel AAV useful for constructing viral vectors. The present invention satisfies this need and provides related advantages as well.

SUMMARY OF THE INVENTION

The present invention provides isolated adenovirus-associated viruses ("adeno-associated viruses" or "AAV"), including a AAV isolates designated AAV3B and AAV6. The invention also provides nucleic acid molecules of AAV3B (SEQ ID NO: 1) or AAV6 (SEQ ID NO: 2), including DNA, which can be an infectious clone, or RNA, and provides proteins encoded by AAV3B or AAV6. For example, the invention provides an AAV3B or an AAV6 infectious clone, which can be in a plasmid containing a p15A replication origin. An AAV nucleic acid molecule of the invention is useful, for example, for constructing AAV viral vectors, which contain an AAV vector genome and can be used to transduce selected host cells with a heterologous nucleic acid sequence, and for constructing AAV vector plasmids, which can be used to transfect cells with a heterologous nucleic acid and which, in combination with AAV helper plasmids, can be used to produce AAV virions, including AAV viral vectors containing an AAV vector genome. The invention also provides AAV3B and AAV6 proteins, which are useful, for example, as antigens for raising antibodies specific for an AAV serotype and as ligands to identify the presence of antibodies specific for the particular proteins.

The invention also provides AAV derived constructs, including AAV viral vectors, which contain an AAV vector genome comprising at least a functional portion of an AAV3B (SEQ ID NO: 1) nucleic acid molecule or a functional portion of an AAV6 (SEQ ID NO: 2) nucleic acid molecule; AAV vector plasmids, which comprise at least a portion of an AAV3B or an AAV6 viral genome and, for example, DNA sequences that allow passage of the vector in a bacterial host cell; and AAV helper plasmids, which provide AAV factors in trans that, in the presence of an AAV vector plasmid, result in production of AAV viral vectors. An AAV viral vector can be a hybrid AAV viral vector, comprising a vector genome of a first AAV serotype such as AAV3B (SEQ ID NO: 1) or AAV6 (SEQ ID NO: 2), and a polypeptide or functional portion of a polypeptide such as a capsid protein of a second AAV serotype, which is different from the first AAV serotype. For example, an AAV viral vector can comprise the inverted terminal repeats of AAV6 (shown as nucleotides 1 to 141 and 4543 to 4683 of SEQ ID NO: 2) and a functional portion of an AAV3B viral genome encoding AAV3B capsid proteins.

The invention further provides vertebrate cells, particularly mammalian cells, containing an AAV3B or AAV6 nucleic acid molecule, or a functional portion thereof. The AAV3B or AAV6 nucleic acid molecule, or functional portion thereof, can comprise an AAV vector genome or an AAV vector plasmid, either of which can contain a heterologous nucleic acid sequence. In addition, the AAV nucleic acid molecule, or functional portion thereof, can encode a functional AAV polypeptide in trans, thus providing a helper function for producing an AAV virion such as an AAV viral vector containing an AAV vector genome. Accordingly, the invention provides an AAV helper cell line, which provides in trans AAV factors that complement the functional cis elements of an AAV vector plasmid and allow the production of AAV viral vectors. Isolated cells containing at least a portion of an AAV viral genome or an AAV vector genome further are encompassed within the present invention, as are the progeny of such cells. A vertebrate cell of the invention can be transduced or transfected in vitro and maintained in vitro; can be transduced or transfected in vitro and administered to a mammal; or can be transduced or transfected in vivo by administration of a functional portion of an AAV nucleic acid molecule to a mammal.

A transduced or transfected mammalian cell of the invention can be used in vitro, for example, to maintain an AAV nucleic acid molecule, including an AAV vector genome, which can contain a heterologous nucleic acid sequence and, therefore, can express a particular polypeptide or RNA molecule. Accordingly, the invention also provides methods of producing a polypeptide or a therapeutic RNA, which can be obtained in a substantially purified form, if desired, and further provides non-human transgenic mammals, which have an AAV3B or an AAV6 nucleic acid molecule, or functional portion thereof, comprising a heterologous nucleic acid molecule, integrated in a chromosome. In addition, a transduced or transfected vertebrate cell of the invention can be a helper cell, which can be used to produce AAV virions containing an AAV vector genome. Thus, the invention provides a method of producing an AAV virion, which contains at least a functional portion of an AAV3B or an AAV6 nucleic acid molecule or a polypeptide encoded thereby, by introducing a functional portion of an AAV nucleic acid molecule into a helper cell, wherein the helper cell provides trans acting factors required for production of an AAV virion.

The invention also provides methods of treating a pathologic condition in a mammal, comprising introducing into the cells of the mammal an AAV viral vector or an AAV vector plasmid containing a heterologous nucleic acid sequence, wherein expression of the heterologous nucleic acid sequence provides a therapeutic benefit to the mammalian cells, specifically, or to the mammal, generally. Such a method of the invention provides a means for treating pathologic conditions, including, for example, cystic fibrosis, cancer, acquired immunodeficiency syndrome (AIDS), atherosclerosis, sickle cell anemia, thalassemia, a blood clotting disorder and diabetes.

The invention also provides AAV3B or AAV6 nucleotide sequences, which can be useful, for example, as probes for identifying the presence of AAV3B or AAV6 nucleic acids in a sample. Such nucleotide sequences of the invention generally comprise at least nine contiguous nucleotides of SEQ ID NO: 1 or SEQ ID NO: 2 and can be used as PCR primers or as hybridization probes, for example, to identify a cell containing an AAV serotype, including AAV3B, AAV6 or a portion thereof, depending on the particular nucleotide sequence of the invention.

The invention further provides a method of identifying an AAV vector useful for treating an individual. This method of the invention is based on the understanding that a mammal that previously has been infected with a particular AAV serotype can be refractory to subsequent infection by that same AAV serotype due, for example, to the generation of neutralizing antibodies by the mammal. Thus, by identifying that a particular mammal previously has been infected by one or more AAV serotypes, the determination can be made that the mammal is best treated using an AAV vector constructed from a different AAV serotype, to which the mammal previously has not been exposed, particularly with an AAV serotype to which the mammal does not produce neutralizing antibodies.

A method of identifying an AAV vector suitable for administration to an individual can utilize, for example, a nucleotide sequence as a hybridization probe to identify the presence of nucleic acids of a particular AAV serotype in a tissue sample obtained from the mammal, where the presence of a particular serotype indicates that a vector comprising a different AAV serotype can be used to introduce the heterologous nucleic acid sequence into the mammal. A method of identifying such an AAV vector also can be performed using antibodies that are specific for a protein expressed by a particular AAV serotype. A method of the invention also can utilize, for example, a particular AAV serotype or a protein such as a capsid protein, or an epitope thereof, from a particular AAV serotype as a probe to identify the presence of antibodies, particularly neutralizing antibodies, in the sample, the presence of such antibodies indicating that a vector comprising a different AAV serotype can be useful for treating the mammal. In addition, a method of identifying a suitable AAV vector also can utilize an AAV virus or AAV viral vector neutralization assay, comprising contacting an AAV serotype or an AAV viral vector containing an AAV vector genome with serum obtained from a subject to be treated and identifying the serotype of those viruses or virions showing a decrease in the functional titer, wherein such a decrease indicates the presence of neutralizing antibodies in the subject and, therefore, that an AAV viral vector of a different serotype, particularly with regard to the viral capsid proteins, is useful for treating the subject.

A panel of nucleotide sequences; or of antibodies specific for a protein expressed by a particular AAV serotype; or of AAV proteins containing epitopes unique for particular AAV serotype or AAV isolate; or of AAV viruses or AAV viral vectors containing an AAV vector genome are particularly useful for screening a sample obtained from a mammal such as a human, such that a suitable AAV viral vector can be selected for introducing a heterologous nucleic acid sequence into the mammal. Thus, the invention provides panels of such AAV nucleotide sequences or antibodies or AAV proteins or AAV viruses containing a viral genome or AAV viral vectors containing an AAV vector genome. If desired, a panel of such reagents can be in the form of a kit, which can facilitate screening a sample obtained from a mammal.

BRIEF DESCRIPTION OF THE DRAWINGS

FIGS. 1(A) through (H) (Parts A–C) shows the complete nucleotide sequences of AAV3B (SEQ ID NO: 1), AAV6 (SEQ ID NO: 2) and AAV2 (SEQ ID NO: 3). Numbers in the left and right margins indicate the nucleotide position for the specified AAV. Dashes are included to maintain sequence homology. Lower case letters indicate nucleotides that are not identical among the three AAV sequences.

Regions of the inverted terminal repeats (ITR) are designated as A, B, C, A' and D at the 5'-end of the sequences and as D, A', B/C, C/B and A at the 3'-end of the sequences. 2, 3B and 6 indicate the terminus of the ITR for AAV2, AAV3B and AAV6, respectively. By analogy to AAV2, the following proposed sites are indicated. Rep binding sites (RBS) and a terminal resolution site (trs) are indicated by a bracket above the binding site. Three viral promoter sites, designated p5 and p19 and p40, also are indicated by brackets above the sequence. The translational start and stop sites of the viral encoded proteins, Rep78/68, Rep52/40, VP1, VP2 and VP3, are indicated by arrows (start sites) and bars (stop sites). The transcription start sites of viral encoded RNA molecules also are indicated by arrows. RNA "splice" sites, including a "minor splice" site; a poly A signal; and the RNA termini also are indicated.

FIGS. 2(A) and (B) shows the amino acid sequences of the capsid protein VP1 for AAV2 (SEQ ID NO: 4), AAV3A (SEQ ID NO: 5), AAV3B (SEQ ID NO: 6), and AAV6 (SEQ ID NO: 7). Numbers in the left and right margins indicate the amino acid position for the specified AAV VP1. The beginning of VP1, as well as the first amino acid of VP2 and VP3, are indicated by an arrow. Boxes indicate amino acid positions that are not identical among the four AAV sequences. Underlined residues indicate differences between AAV3A and AAV3B.

Figure 3:
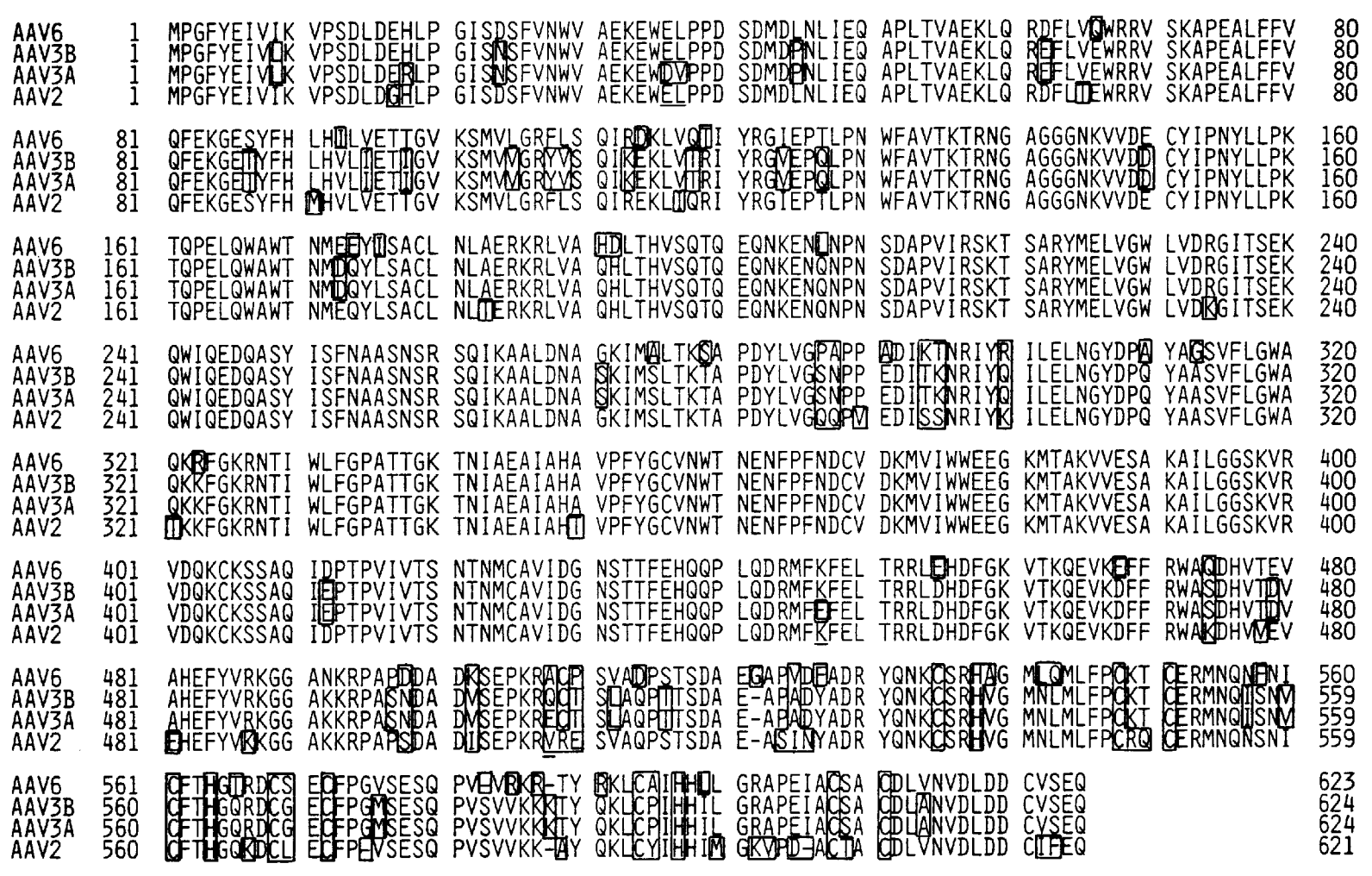

FIG. 3 shows the amino acid sequences of the Rep78 proteins for AAV2 (SEQ ID NO: 8), AAV3A (SEQ ID NO: 9), AAV3B (SEQ ID NO: 10), and AAV6 (SEQ ID NO: 11). Numbers in the left and right margins indicate the amino acid position for the specified AAV VP1. Dashes are included to maintain sequence homology. Boxes indicate amino acid positions that are not identical among the four AAV sequences. Underlined residues indicate differences between AAV3A and AAV3B.

Figure 4:
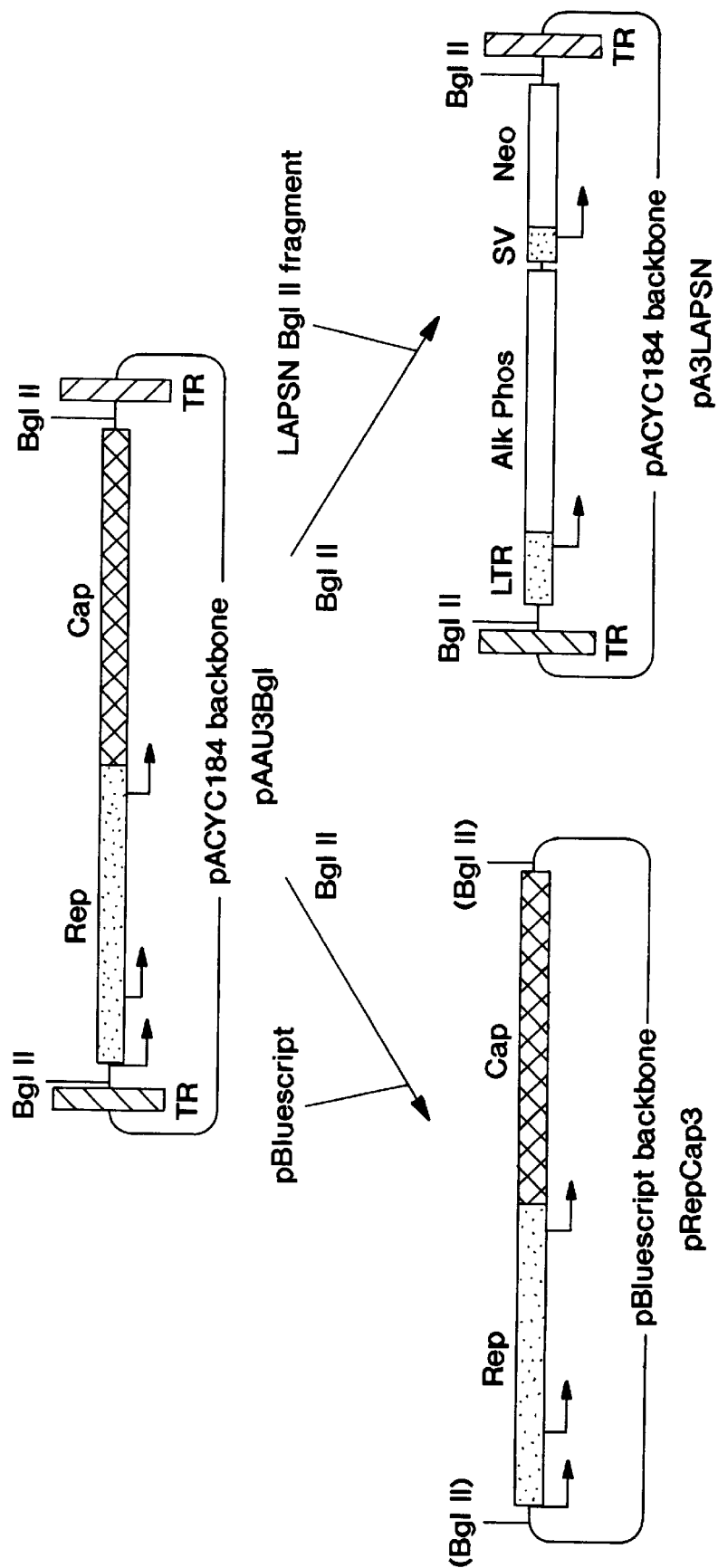

FIG. 4 illustrates the construction of an AAV3B vector plasmid (pA3LAPSN) and AAV3B helper plasmid (pRepCap3) from an AAV3B infectious clone (pAAV3Bgl; see Example III for details).

Figure 5:
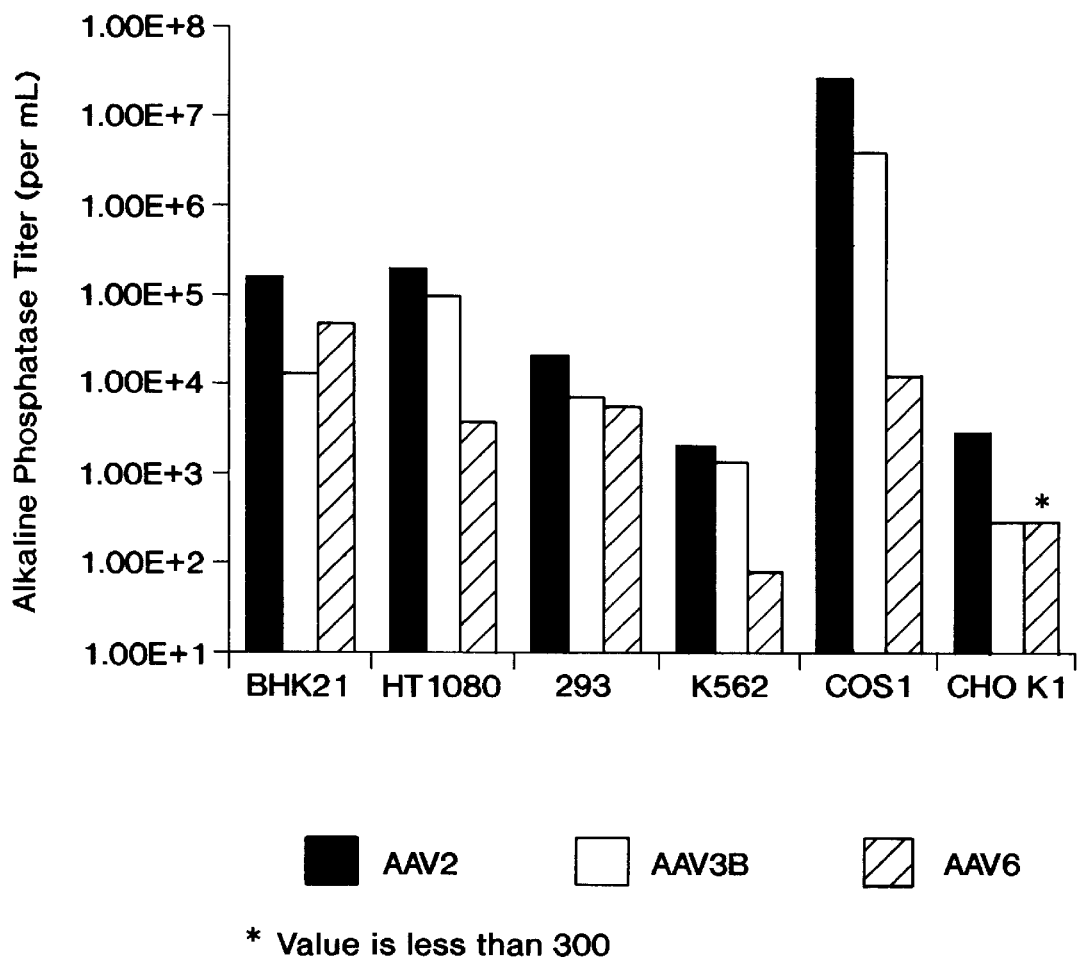

FIG. 5 illustrates the host range specificity of AAV viral vectors. AAV2 (solid bars), AAV3B (open bars) and AAV6 (hatched bars) viral vectors were used to transduce the various cell lines, as indicated (see Example III), and titer of alkaline phosphatase was determined.

DETAILED DESCRIPTION OF THE INVENTION

The present invention provides isolated adenovirus-associated viruses ("adeno-associated viruses" or "AAV"), including AAV isolates designated AAV3B and AAV6. As used herein, the term "adeno-associated virus" or "AAV" means a member of Dependovirus genus of the Parvoviridae family of viruses. This genus of parvoviruses is characterized by a dependence on a helper virus for complete AAV replication and by the ability to stably integrate into a host cell chromosome in the absence of helper virus (for review, see Muzyczka, Curr. Topics Microbiol. Immunol. 158:97–129 (1992)).

As used herein, the term "isolated," when used in reference to an AAV, means that the viral particle is enriched with respect to the cellular material of the host cell that the virus normally is associated with in nature. An isolated AAV can be obtained, for example, by cesium chloride gradient centrifugation, wherein the isolated AAV can be obtained by collecting the fraction having a density of 1.40 to 1.41 g/cc (see Example I).

The invention also provides a substantially purified AAV3B viral genome, which is a nucleic acid molecule having the nucleotide sequence shown as SEQ ID NO: 1 (see, also, Example II). In addition, the invention provides a substantially purified AAV6 viral genome, which is a nucleic acid molecule having the nucleotide sequence shown as SEQ ID NO: 2. As used herein, the term "substantially purified," when used in reference to an AAV nucleic acid molecule, means that the nucleic acid molecule comprising the viral genome is free from the relevant viral particle. Such a substantially purified nucleic acid molecule can be prepared using routine methods such as gradient centrifugation following disruption of the viral particle and can be single stranded or double stranded (see Samulski et al., J. Virol. 63:3822–38 (1989); Tamayose et al., Hum. Gene Ther. 7:507–513 (1996), each of which is incorporated herein by reference).

In particular, the present invention provides infectious clones of an AAV3B nucleic acid molecule (SEQ ID NO: 1) or an AAV6 nucleic acid molecule (SEQ ID NO: 2; see Example I). As used herein, the term "infectious clone" means a nucleic acid molecule of an AAV3B or an AAV6 viral genome that, upon introduction into a mammalian cell, results in the production of AAV virions by the cell. An infectious clone of an AAV3B or AAV6 can be maintained as a linear nucleic acid molecule or can be inserted into a plasmid to facilitate manipulation of the infectious clone (Laughlin et al., Gene 23:65–73 (1983), which is incorporated herein by reference). An infectious clone can be introduced into a mammalian cell using routine methods of transfection, including, for example, lipofection, electroporation, particle mediated transfer or the like. Introduction of an infectious clone of AAV3B or AAV6 into a mammalian cell also provides a convenient means of producing AAV3B or AAV6 viral particles, respectively.

Figure 1A:
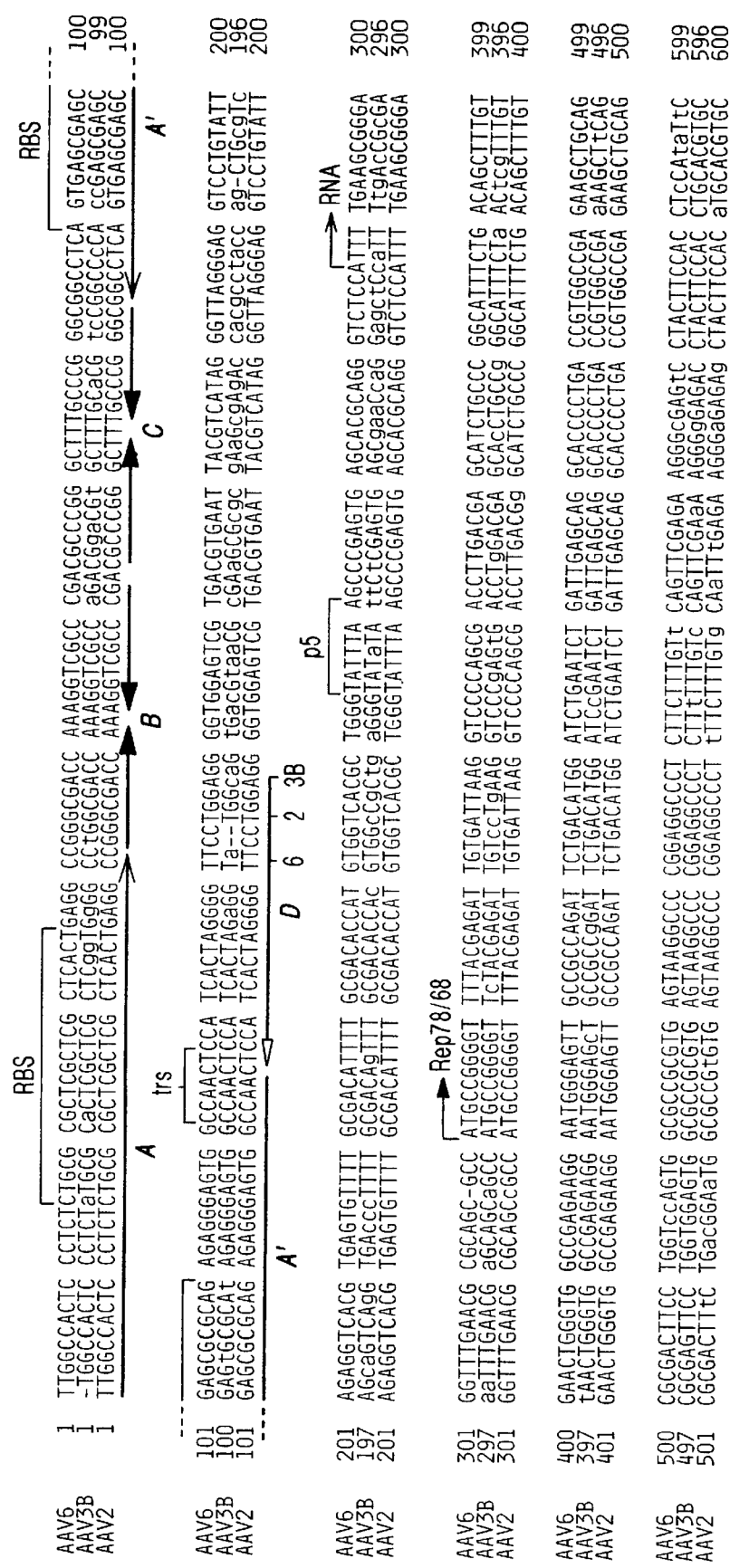
Figure 1B:
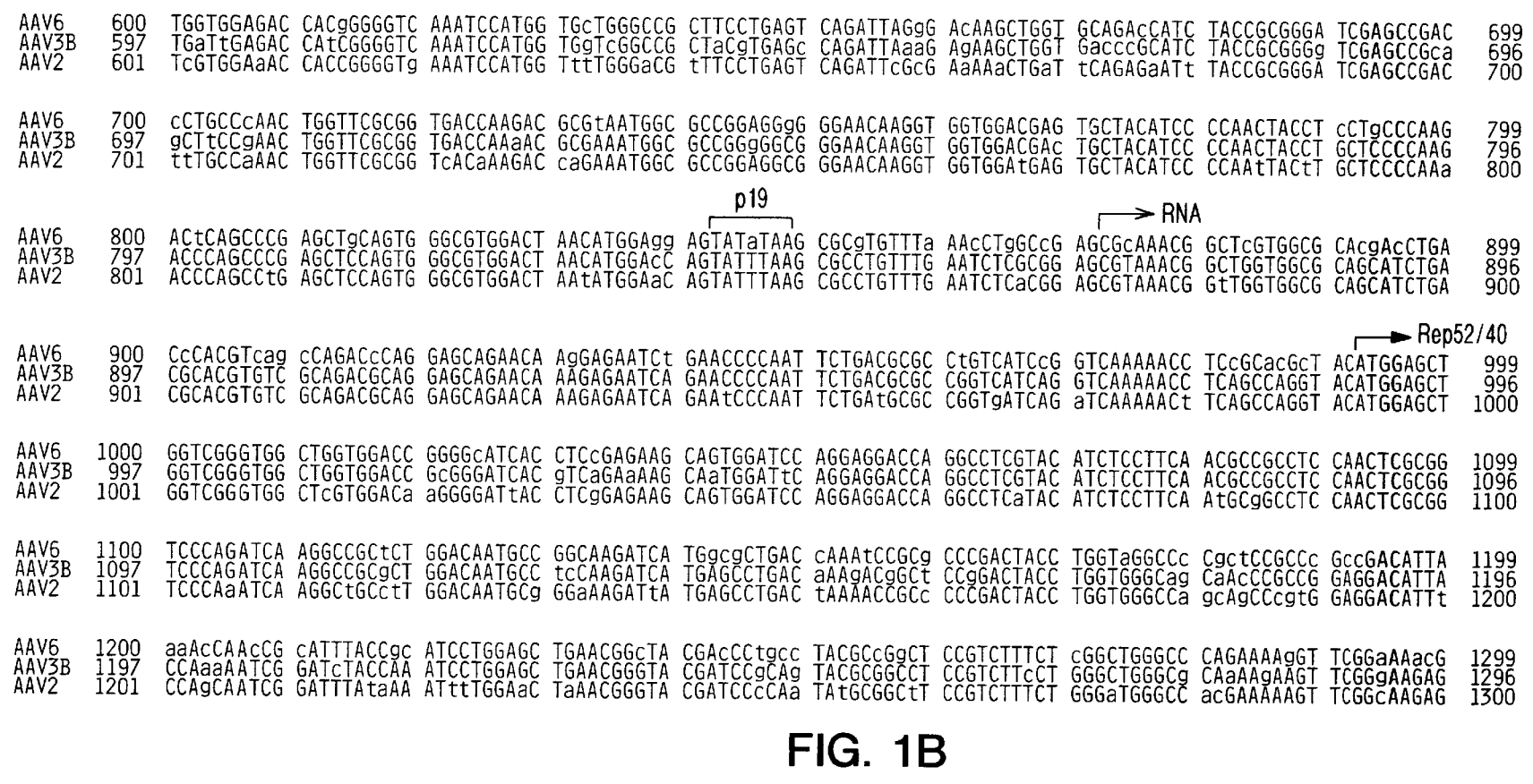
Figure 1C:
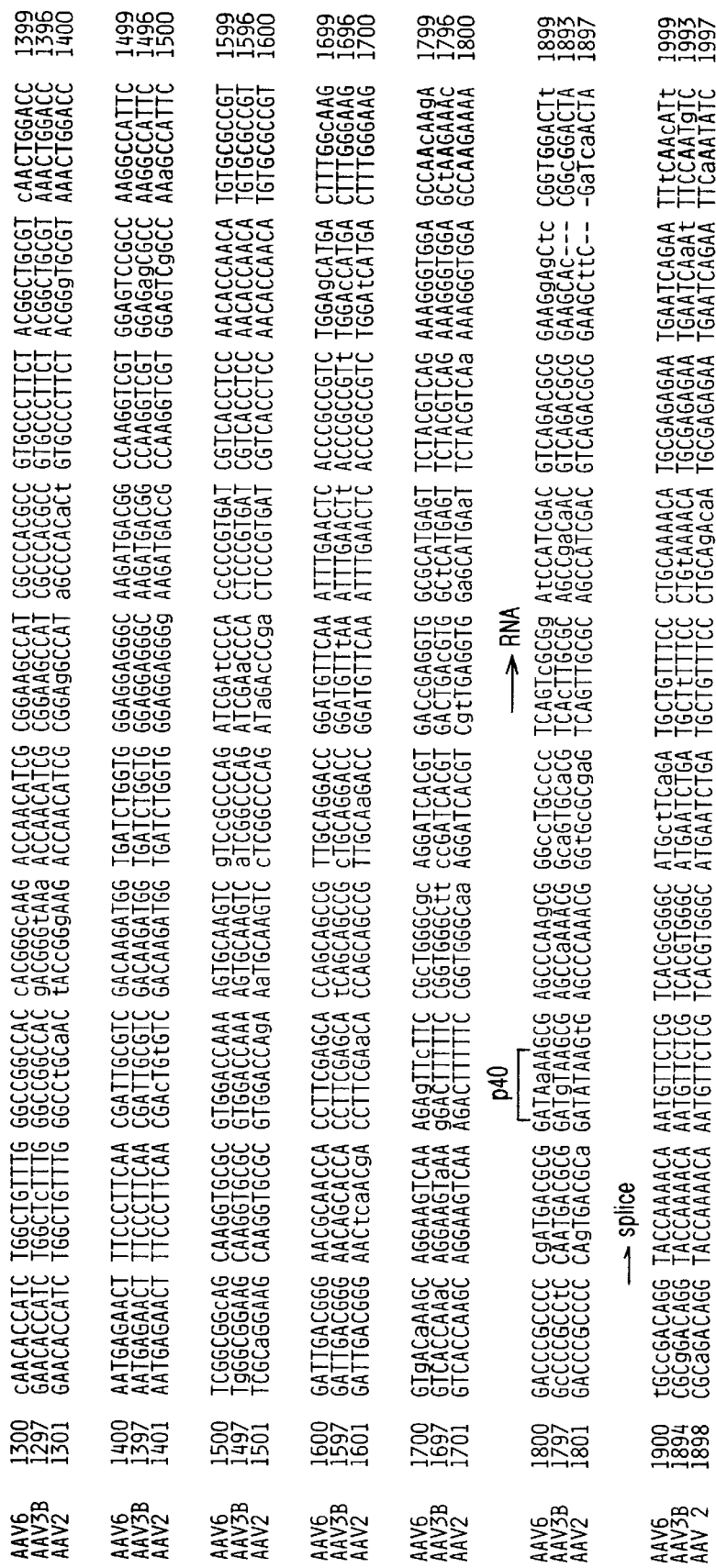
Figure 1D:
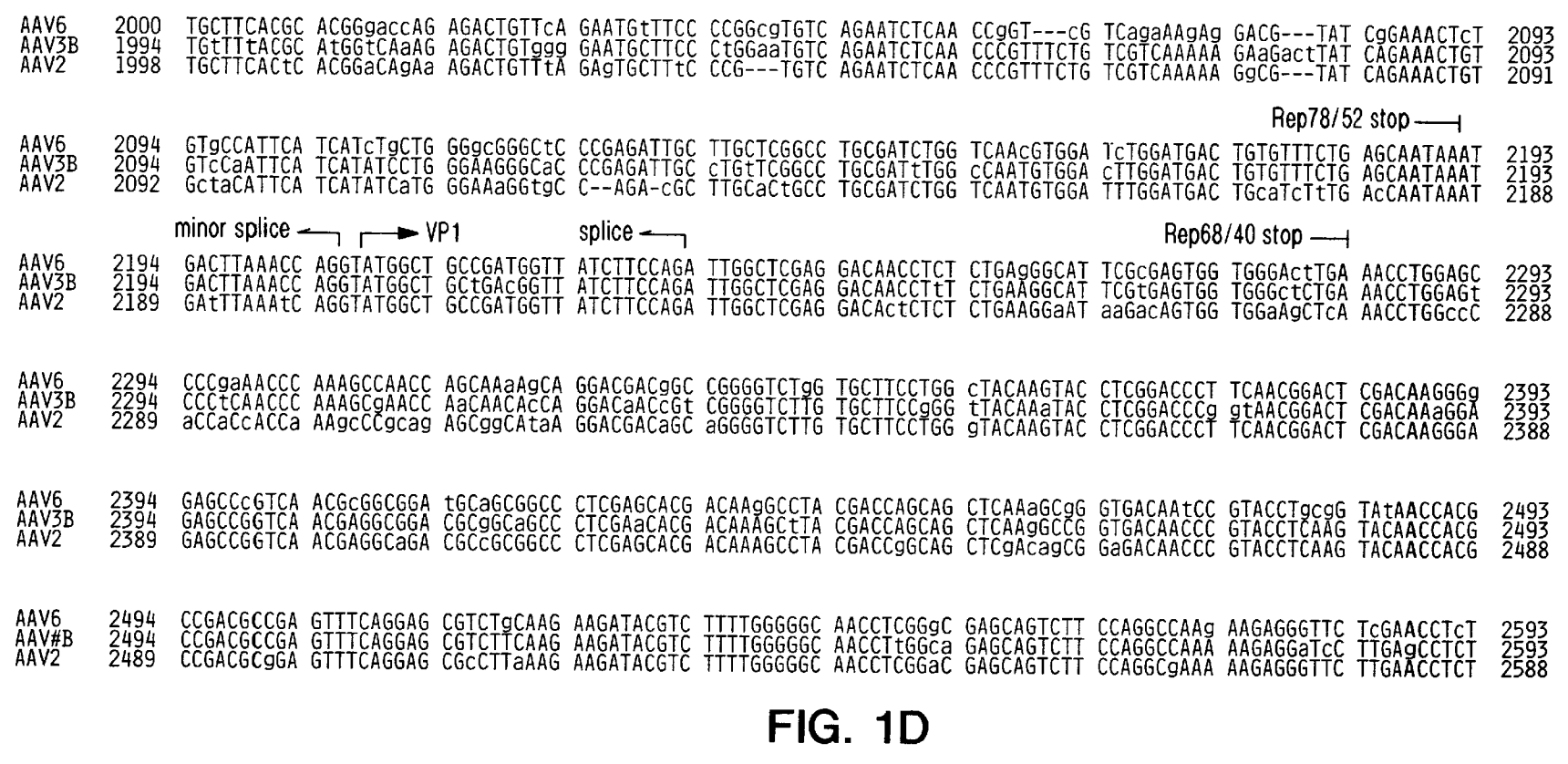
Figure 1E:
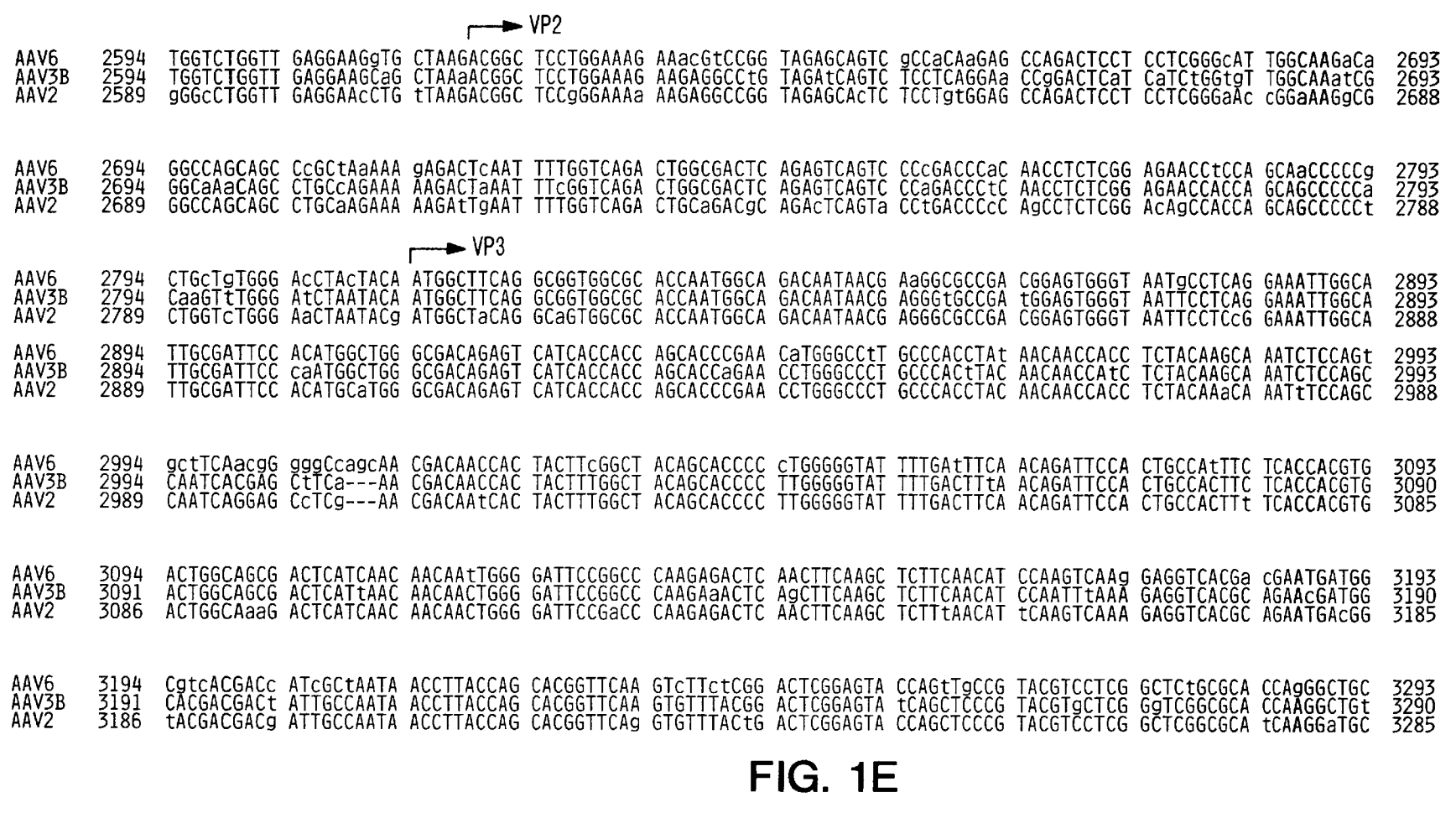
Figure 1H:
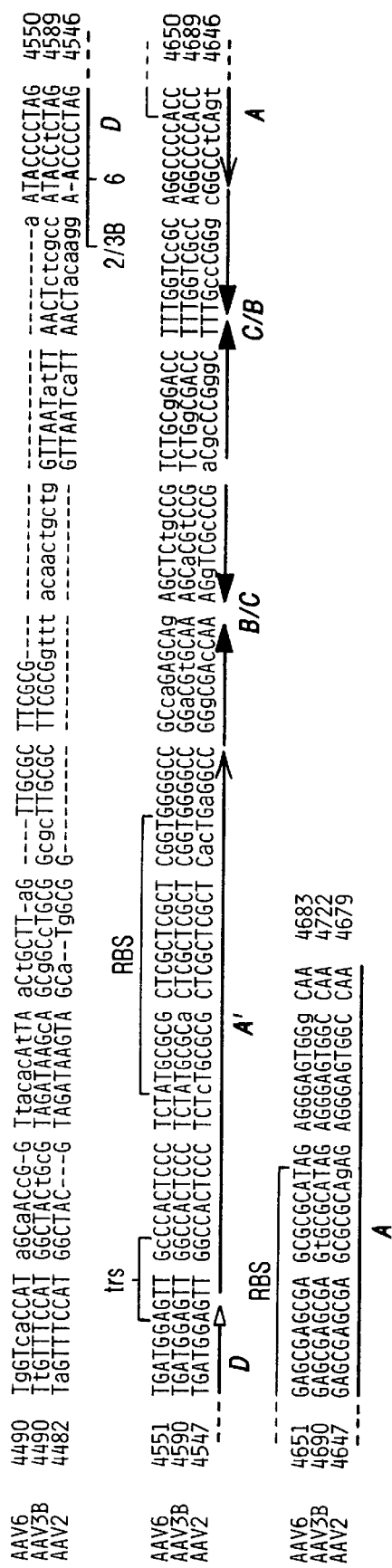

Prior to the present disclosure, five serotypes of AAV, designated AAV1, AAV2, AAV3, AAV4 and AAV5, were known. A previously unknown AAV isolate, which has the characteristics expected of a distinct AAV serotype, is disclosed herein (FIG. 1, SEQ ID NO: 2). Based on its nucleotide sequence divergence from AAV2 (SEQ ID NO: 3), the newly disclosed AAV is designated AAV6 (SEQ ID NO: 2), although classification of AAV6 as a distinct serotype awaits serological characterization. In view of this caveat, AAV6 nevertheless is referred to as a serotype for purposes of the present discussion. In addition, a previously undescribed AAV3 isolate, designated AAV3B, is disclosed herein (SEQ ID NO: 1; FIG. 1). In view of the present disclosure of AAV3B, the previously identified AAV3 isolate is referred to herein as "AAV3A" (see Muramatsu et al., Virology 221:208–217 (1996)).

As used herein, the term "serotype," when used in reference to AAV, means a subdivision of AAV that is identifiable by serologic or DNA sequencing methods and can be distinguishable by its antigenic character. In addition, the term "isolate," when used in reference to AAV, means a particular AAV serotype obtained from a specific source. The skilled artisan readily will recognize the difference between an "isolated AAV," which refers to the relative purity of an AAV sample, and an "AAV isolate," which refers to a clonally derived preparation of a particular AAV serotype, based on the context in which the term is used.

Although different AAV isolates of a particular serotype can have identical sequences over portions of their genomes, such isolates are not necessarily identical, but share substantial nucleotide sequence identity. For example, the nucleotide sequence of the disclosed AAV3B isolate (FIG. 1; SEQ ID NO: 1) of AAV3 differs from the previously described AAV3A at 17 nucleotide positions (see Table 1; see, also, Muramatsu et al., supra, 1996). Due to these sequence differences, AAV3B polypeptides such as the viral capsid protein, VP1, can have a different amino acid sequence from AAV3A VP1 and, therefore, can be antigenically distinguishable from AAV3A (see FIG. 2, compare amino acid position 598 of AAV3A and AAV3B; see, also, FIG. 3, compare amino acid position 508 of AAV3A and AAV3B Rep proteins).

these sequences confer serotype-specific functions, including host cell specificity. In particular, the capsid proteins likely are targets for neutralizing antibodies that are generated by a host in response to AAV infection. For example, peptide portions of VP1 of the various AAV serotypes are particularly variable around amino acids 20 to 43, amino acids 450 to 480, amino acids 545 to 559, amino acids 580

TABLE 1

AAV3B AND AAV3A Sequence Differences

Position in Genome (AAV3 numbering)

| Virus | 1 | 370 | 425 | 426 | 1656 | 1839 | 2638 | 2641 | 2739 | 3170 | 3173 | 3988 | 4000 | 4418 | 4484 | 4490 | 3' ITR |
|---|---|---|---|---|---|---|---|---|---|---|---|---|---|---|---|---|---|
| AAV3B | Δ | A | G | C | A | C | A | C | C | A | A | A | G | Δ | Δ | Δ | FLIP |
| AAV3A | T | G | C | G | G | G | G | G | A | G | G | G | C | G | T | T | FLOP |

Notes
Flip and Flop are ITR orientations
A, C, G, and T are nucleotide bases at the indicated positions
Δ means deletion of nucleotide AAV is a nonenveloped virus that is icosohedral and is about 20 to 24 nm in diameter with a density of 1.40–1.41 g/cc. AAV viruses contain a single stranded linear genomic DNA molecule approximately 4.7 kilobases (kb) in length (see FIG. 1). The single stranded AAV genomic DNA consists of either a plus strand or a minus strand, each of which is packaged with equal efficiency and is equally infectious.

AAV2, which is the best characterized AAV serotype, contains a single stranded linear genome having 4679 nucleotides (FIG. 1; SEQ ID NO: 3; see, also, Srivastava et al., *J. Virol.* 45:555–564 (1983), which is incorporated herein by reference). The AAV3A viral genome also has been sequenced and shares 82% homology with AAV2 (Muramatsu et al., supra, 1996). As disclosed herein, the AAV3B and AAV6 genomes share approximately 82–85% homology with AAV2 (see FIG. 1; see, also, FIG. 2). The sequences of AAV1, AAV4 and AAV5 have not been reported.

AAV genomic DNA contains inverted terminal repeats (ITR's) at each end. Each ITR is about 141 to 146 nucleotides in length (see FIG. 1). The first 125 nucleotides of an ITR form a T-shaped hairpin structure composed of two small internal palindromes (formed by "B" and "C" in FIG. 1) flanked by a larger palindrome ("A"). The ITR sequences are required in cis for AAV replication and for rescue or excision from prokaryotic plasmids and contain the minimal sequence required for AAV proviral integration and for packaging into virions (Muzyczka, supra, 1992).

In addition to the ITR's, AAV genomic DNA contains non-coding sequences 5' to the Rep coding sequence and 3' to the polyadenylation site (FIG. 1). The 5' non-coding sequence of AAV3B, for example, which includes the p5 promoter, contains several nucleotide substitutions unique to the AAV3B serotype, indicating that nucleotide sequences based on the non-coding region can be useful as probes for identifying the presence of AAV3B (see Table 1). The 3' non-coding sequence, which is about 80 to 120 nucleotides, depending on the AAV serotype, varies significantly among AAV2, AAV3B and AAV6. The degree of variation in the 3' non-coding region indicates the region may be involved in serotype-specific cis acting functions.

Variable regions are present within the capsid proteins (see FIG. 2) and Rep proteins (see FIG. 3), indicating that to 600, and others as can be identified by inspection of FIG. 2 (compare SEQ ID NOS: 4–7). Thus, peptide portions of an AAV3B or an AAV6 comprising these amino acid sequences can be particularly useful for raising antibodies, for example, to an AAV serotype present in a sample. In addition, such peptide portions of the different AAV serotypes can be used to identify the presence of antibodies in an individual infected by AAV. Such peptide portions of an AAV polypeptide also can be incorporated into viral capsids to confer specific functions.

Fully permissive AAV infection requires the presence of an adenovirus or herpesvirus helper virus, although vaccinia virus also can provide some helper functions (Muzyczka, supra, 1992). In the absence of a helper virus, AAV produces no progeny virus but, instead, can integrate into a host chromosome. However, if a cell carrying an AAV provirus subsequently is superinfected with a helper virus, the AAV genome is excised and proceeds through a normal productive infection. The helper virus genes do not appear to be directly involved in AAV DNA replication but, instead, appear to maximize the synthesis of the AAV encoded gene products or of cellular genes required for AAV DNA replication. Such a role for the helper virus genes is supported by evidence that a small percentage of cells can become fully permissive for AAV DNA replication, in the absence of helper virus, if the cells are transformed with either a viral or a cellular oncogene and if the cells are synchronized or treated with an agent such as hydroxyurea or UV irradiation, which transiently arrests cellular DNA synthesis (Muzyczka, supra, 1992).

In vivo experiments indicate that brain and muscle cells are transduced efficiently by AAV2 vectors (Alexander et al., *Human Gene Ther.* 7:841–850 (1996); Xiao et al., *J. Virol.* 70: 8098–8108 (1996), each of which is incorporated herein by reference). However, low transduction rates were observed in mouse liver and lung cells in the absence of either adenoviral helper functions (Fisher et al., *Blood* 88:492–504 (1996), which is incorporated herein by reference) or prior treatment with agents affecting DNA metabolism (Koeberl et al., *Proc. Natl. Acad. Sci., USA* 94:1426–1431 (1997), which is incorporated herein by reference), although rabbit lung was transduced efficiently (Flotte et al., *Proc. Natl. Acad. Sci., USA* 90:10613–10617 (1993), which is incorporated herein by reference), suggesting an interspecies variation in transduction efficiency. In addition, transduction rates vary within a single organ, for example, in brain, where pia arachnoid and choroid epithelial cells were most efficiently transduced (Alexander et al., supra, 1996).

Variable transduction rates have also been observed in vitro. In the case of human fibroblasts, for example, AAV2 vectors preferentially transduce S phase cells as compared to quiescent cells (Russell et al., *Proc. Natl. Acad. Sci., USA* 91:8915–8919 (1994), which is incorporated herein by reference), and immortalized cells as compared to normal cells (Halbert et al., *J. Virol.* 69:1473–1479 (1995), which is incorporated herein by reference). In contrast, hematopoietic cells including primary hematopoietic progenitors require MOI's of $1 \times 10^7$ or more vector particles per cell to detect transgene expression, an MOI four logs higher than that required to transduce HeLa cells (Bertran et al., *J. Virol.* 70:6759–6766 (1996); Hargrove et al., *Blood* 89:2167–2175 (1997), each of which is incorporated herein by reference). Some human leukemia cell lines also were non-permissive for AAV2 infection (Mizukami et al., *Virology* 217:124–130 (1996); Ponnazhagan et al., *J. Gen. Virol.* 77:1111–1122 (1996)).

The variability of AAV2 infectivity can be due to different expression patterns of a receptor molecule, which is used by AAV2 for entry into cells. Although an AAV2 receptor gene has not been cloned, a 150 kiloDalton (kDa) glycoprotein is a candidate cell surface receptor that binds to the virus (Mizukami et al., supra, 1996). This 150 kDa protein was not detected in cells resistant to AAV2 infection (Mizukami et al., supra, 1996), indicating that expression of the receptor determines host range. Furthermore, inhibition of binding of labeled AAV2 by unlabeled AAV2 virions, but not by AAV1 or AAV3 virions, is consistent with the use of different receptors by each AAV serotype and indicates that the variability in AAV capsid protein amino acid sequences can determine, in part, the particular receptor bound by an AAV serotype, as well as the specificity of an immune response generated by the host. Thus, as disclosed herein, the host range of an AAV viral vector can be modified, for example, by incorporating into the AAV viral vector all or a portion of a different AAV serotype capsid protein, thereby producing a hybrid AAV viral vector.

Analogous to the present disclosure regarding AAV serotypes, the host range of retroviral vectors comprising various retroviral pseudotypes varies considerably and is largely determined by functional receptor levels (Miller, *Proc. Natl. Acad. Sci., USA* 93:11407–11413 (1996)). In the case of hematopoietic stem cells, for example, the choice of retroviral vector pseudotype is important because low amphotropic receptor expression limits stem cell transduction by amphotropic vectors, while higher expression of the ecotropic receptor correlates with improved ecotropic vector transduction rates (Orlic et al., *Proc. Natl. Acad. Sci., USA* 93:11097–11102 (1996)). Receptor levels can also vary with cell proliferation as observed for the ecotropic retrovirus receptor, which can affect transduction rates in quiescent cells. The development of a set of AAV viral vector serotypes using different receptors would increase the potential of this vector system, as was the case for the different retroviral vector pseudotypes.

The variability in host cell specificity and the generation of a viral neutralizing host immune response currently limit the usefulness of AAV2 as a vector for gene therapy and no vectors based on other AAV serotypes have been described. Infection by wild type AAV elicits a strong immune response in humans, which includes the production of neutralizing and complement fixing antibodies (Blacklow et al., *J. Natl. Cancer Inst.* 40:319–327 (1968); Georg Fries et al., *Virology* 134:64–71 (1984)). Approximately 50% to 85% of adults have neutralizing antibodies to AAV, with antibodies against AAV2 being the most predominant serotype. Although the effects of these antibodies on in vivo gene transfer have not been studied in humans, the presence of high titer neutralizing antibody likely decreases the transduction efficiency by an AAV serotype in human populations. In this regard, additional transduction events are not observed after readministration of AAV2 vectors in mice, indicating that the host immune response can completely prevent transduction (Xiao et al., supra, 1996).

The identification of AAV3B and AAV6 provide a means to overcome the limitations created by having only vectors based on AAV2 available. For example, the capsid protein variability of AAV3B and AAV6 with respect to AAV2 and AAV3A indicates that AAV3B and AAV6 can be used to construct AAV viral vectors that have a host cell specificity different from that of AAV2. In addition, the disclosure that AAV3B and AAV6 can be used to produce AAV viral vectors, as well as AAV vector plasmids and AAV helper plasmids, can be extended to AAV3A, thus allowing the construction of vectors and plasmids based, at least in part, on AAV3A. Furthermore, the availability of AAV viral vectors based on AAV3A, AAV3B or AAV6 provides an opportunity to use such vectors in patients that previously have generated a viral neutralizing immune response against AAV2. Accordingly, combinations of cis and trans acting components of one or more AAV serotypes, particularly AAV3B or AAV6, are used to produce AAV viral vectors and AAV vector plasmids and AAV helper plasmids having desirable characteristics.

The viral genomes of AAV3B (SEQ ID NO: 1) and AAV6 (SEQ ID NO: 2) are useful for constructing AAV viral vectors and AAV vector plasmids, which can be used to introduce a heterologous nucleic acid sequence into a selected population of cells, and AAV helper plasmids, which express AAV trans acting factors (see Example III). As used herein, the term "viral genome," when used in reference to AAV, means the full length nucleic acid molecule found in the wild-type virus. It is recognized that an AAV viral genome is a single stranded nucleic acid molecule, which can be the plus strand or the minus strand, but that the combination of plus and minus strands in solution results in hybridization of the complementary strands to produce a double stranded form of the AAV viral genome. In addition, a viral genome can be in a double stranded form, which can be contained in plasmid.

In addition, the term "vector genome" is used herein in reference to the single stranded nucleic acid molecule that is derived from an AAV viral genome and comprises at least a functional portion of the AAV viral genome. For example, reference to an "AAV6 vector genome" means that the vector genome is derived from and, therefore, contains at least a functional portion of an AAV6 viral genome. It is recognized, however, that a vector genome such an AAV6 vector genome as exemplified above, for example, also can contain portions of a viral genome from an AAV isolate other than AAV6, thus producing a hybrid vector genome, and that an AAV viral vector containing such an AAV6 vector genome can contain AAV6 viral proteins or can contain viral proteins of a different AAV isolate or serotype, thus producing a hybrid AAV viral vector. A vector genome can be in a double stranded form, which can be contained in a plasmid.

In general, an AAV vector genome is present in an AAV viral vector of the invention or is present in a cell transduced by such a viral vector or in a helper cell containing an AAV vector plasmid. In this regard, it is recognized that an AAV vector genome, while single stranded when present in an AAV viral vector, is converted into a double stranded nucleic acid molecule in a host cell, particularly when stably integrated into the host cell genome, and, therefore, can be in a double stranded form in host cells and in progeny cells derived therefrom.

As used herein, the term "AAV viral vector" means an AAV viral particle containing an AAV vector genome. If desired the polypeptide components of the AAV viral particle can be from the same AAV serotype as the vector genome or can be from a different serotype, thus producing a hybrid AAV viral vector. Furthermore, a polypeptide component of a hybrid AAV viral particle can be hybrid viral protein, for example, a hybrid capsid protein, which can consist of a portion of a capsid protein of a first AAV serotype and a portion of a capsid protein of a second, different AAV serotype. In particular, a hybrid capsid can be constructed so as to lack one or more epitopes recognized by neutralizing antibodies, thereby allowing administration of an AAV viral vector comprising the hybrid capsid protein to an individual having neutralizing antibodies to a particular AAV serotype. Accordingly, the present invention provides AAV viral vectors comprising at least a portion of an AAV3B or an AAV6 polypeptide, as well as AAV viral vectors comprising a vector genome containing a functional portion of an AAV3B or an AAV6 viral genome.

In general, the vector genome of an AAV viral vector contains a heterologous nucleic acid sequence and, therefore, an AAV viral vector can be useful for transducing mammalian cells with the heterologous nucleic acid sequence. Since an AAV viral vector contains a single stranded nucleic acid molecule within the virion, the viral vector itself is not necessarily manipulated, for example, to insert a heterologous nucleic acid sequence, but is produced in a helper cell containing an AAV vector plasmid, the appropriate AAV trans acting factors, and an appropriate helper virus.

The term "AAV vector plasmid" is used herein to mean a double stranded circular nucleic acid molecule that contains at least a functional portion of an AAV nucleic acid molecule. Generally, an AAV vector plasmid also contains a functional portion of a bacterial plasmid nucleic acid sequence, and is suitable for insertion of a heterologous nucleic acid sequence. An AAV vector plasmid can be used to transfect a cell with a heterologous nucleic acid sequence. An AAV vector plasmid provides the advantage that it can be propagated in an appropriate bacterial host cell and that it can be readily manipulated using routine methods of recombinant DNA technology (see, for example, Bartlett et al., in "Protocols for Gene Transfer in Neuroscience: Towards Gene Therapy of Neurological Disorders" (John Wiley & Sons Ltd. 1996), chap. 9; Tratschin et al., *Mol. Cell. Biol.* 5:3251–3260 (1985); Laughlin et al., *Gene* 23:65–73 (1983), each of which is incorporated herein by reference). In addition, when an AAV vector plasmid is present in a cell with an appropriate AAV helper plasmid and a helper virus, AAV viral vectors are produced based on the AAV vector plasmid.

An AAV vector plasmid of the invention generally contains a functional portion of a nucleic acid molecule of an AAV serotype, particularly AAV3B or AAV6, and a bacterial origin of replication. In addition, an AAV vector plasmid can contain a gene that confers a selective advantage to a cell containing the vector; for example, the vector plasmid can express a gene product that confers antibiotic resistance. An AAV vector plasmid also can contain a multiple cloning site to facilitate insertion of a heterologous nucleic acid molecule into the vector.

An AAV vector plasmid, including a heterologous nucleic acid sequence, can be any size from several hundred base pairs up to several thousand base pairs, although manipulation of such a plasmid becomes inconvenient as the size increases. Such an AAV vector plasmid can be transfected into a host cell and, where the cell expresses an AAV Rep protein, ITR's in the vector plasmid can direct integration into the host cell genome such that the heterologous nucleic acid sequence can be stably expressed. If desired, the Rep protein can be a component of the AAV vector plasmid, from which it is expressed; can be expressed from a second plasmid, which is cotransfected with the AAV vector plasmid; or can be stably transfected in the host cell.

An AAV vector plasmid is particularly useful for producing an AAV viral vector by transfecting the AAV vector plasmid into an appropriate helper cell, although AAV viral vectors also can be produced by transducing an AAV viral vector into the helper cell. As used herein, the term "helper cell," when used in reference to AAV, means a cell that expresses the requisite AAV trans acting factors, which the AAV vector plasmid or AAV viral vector lacks, and that can be infected with a helper virus such as an adenovirus or herpesvirus. Helper cells conveniently can be utilized as a source of a particular AAV polypeptide such as an AAV capsid or Rep protein.

A helper cell is selected based, in part, on its ability to become infected by an appropriate helper virus, particularly an adenovirus or herpesvirus, which is required for the production of infective AAV virions. Thus, a helper cell is selected, in part, based on its ability to be infected by a helper virus. Examples of cells that can be used as helper cells include, for example, Cos cells, HeLa cells or human kidney derived 293 cells (see Example III). In addition, a helper cell is transfected with a helper plasmid, which contains functional AAV nucleic acid sequences encoding the requisite AAV trans acting factors. As used herein, the term "AAV helper plasmid" means a plasmid that contains AAV nucleic acid sequences encoding trans acting factors that complement the AAV sequences present in cis in an AAV vector plasmid or an AAV viral vector, such that an AAV viral vector containing an AAV vector genome can be produced.

A helper cell that produces viral vectors can be produced by cotransfecting an AAV helper plasmid into a cell with an AAV vector plasmid or an AAV viral vector. In addition, a helper cell can be produced by stably transfecting an AAV helper plasmid, particularly the functional AAV nucleic acid sequences encoding the trans acting factors, into the cell (Clark et al., *Hum. Gene Ther.* 6:1329–1341 (1995), which is incorporated herein by reference). The availability of a stably transfected helper cells eliminates the need to cotransfect a helper plasmid and vector plasmid in order to produce AAV viral vectors. Since the efficiency of cotransfection of a cell is relatively low, the use of stably transfected helper cells increases the number of AAV trans acting factor-producing helper cells that also are transfected with an AAV vector plasmid, thereby increasing the titer of AAV viral vectors produced. Helper cells expressing particular AAV serotype capsid proteins, for example, can be particularly useful because the helper cells can be used to produce AAV viral vectors having an appropriate antigenicity so as to avoid neutralizing antibodies expressed by an individual.

Upon introducing an AAV vector plasmid and an AAV helper plasmid, for example, into an adenovirus infected helper cell, an AAV viral vector containing an AAV vector genome is produced. The AAV vector genome represents a single stranded version of the AAV nucleic acid sequences and heterologous nucleic acid sequence, if present, that were present in the AAV vector plasmid from which it was produced, except that the AAV vector genome lacks the plasmid backbone sequences. In particular, the AAV vector genome contains AAV ITR's and, generally, an inserted heterologous nucleic acid sequence (see Example III). For example, the AAV helper plasmid can encode the trans acting AAV3B Rep and Cap proteins and the AAV vector plasmid can contain AAV6 ITR's flanking a heterologous nucleic acid sequence. Upon cotransfection of the AAV vector plasmid and the AAV helper plasmid into adenovirus infected cells, an AAV viral vector is produced, wherein the viral capsid is composed of AAV3B capsid proteins and the AAV vector genome is composed of AAV6 ITR's containing the inserted heterologous nucleic acid sequence.

Where an AAV vector plasmid is to be used to generate AAV viral vectors, which include an AAV vector genome packaged into an AAV viral particle, the size of the AAV vector genome, including any functional AAV sequences and inserted heterologous nucleic acid sequences, can have a size that is as small as about 1 kb or as large as about 6 kb. It is recognized, however, that packaging of an AAV vector genome is more efficient if the AAV sequences and inserted heterologous sequence total about 2 kb to about 5 kb and is most efficient if the total size of the AAV vector genome, including inserts, is about 2.5 kb to about 4.5 kb. In comparison, an AAV vector plasmid, including heterologous nucleic acid sequences, can be much larger in size, since the plasmid is not all packaged into a viral particle.

As used herein, the term "heterologous," when used in reference to a nucleic acid sequence, or to an RNA or polypeptide encoded thereby, means that the nucleic acid sequence, or the RNA or polypeptide, is from an organism other than AAV or is synthetically derived. Thus, a heterologous nucleic acid sequence can be from a prokaryotic or eukaryotic organism and can encode a polypeptide such as an enzyme, a structural protein, an antibody or other polypeptide of interest or can encode an RNA having a structural or therapeutic function.

An AAV viral vector of the invention can be a hybrid AAV viral vector, which comprises a first functional portion of an AAV3B (SEQ ID NO: 1) or an AAV6 (SEQ ID NO: 2) nucleic acid molecule and a second functional portion of a viral genome of an AAV serotype that is different from the serotype from which the first functional portion was obtained. Thus, a hybrid AAV vector of the invention can comprise, for example, the inverted terminal repeats of AAV3B (nucleotides 1 to 146 and nucleotides 4578 to 4722 of SEQ ID NO: 1) or of AAV6 (nucleotides 1 to 141 and nucleotides 4543 to 4683 of SEQ ID NO: 2) and a Rep78 protein coding sequence (nucleotides 321 to 2186 of SEQ ID NO: 3) or a promoter sequence of AAV2 (see FIG. 1). Similarly, a hybrid AAV viral vector can be constructed containing, for example, AAV3B capsid proteins and a vector genome containing AAV6 ITR's or a hybrid capsid protein comprising, for example, a portion of an AAV6 capsid protein and a portion of an AAV2 capsid protein, such that a functional capsid protein is produced. Such hybrid AAV viral vectors are produced using the appropriate AAV vector plasmids and helper plasmids.

As used herein, the term "functional portion," when used in reference to an AAV nucleic acid molecule, means an AAV nucleotide sequence having a defined function, which can be a regulatory function or a coding function. A functional portion of an AAV, for example, can be a nucleotide sequence comprising an AAV ITR, or can encode an AAV Rep protein or capsid protein or a peptide portion of such a protein, or can provide a Rep binding site (RBS) or terminal resolution site (trs) or an RNA splice site or polyadenylation signal (see FIG. 1). In addition, the terms "first" and "second," when used in reference to a functional portion of an AAV nucleic acid molecule, mean that the functional portions are from an AAV of one serotype or isolate ("first") and an AAV of a second, different serotype or isolate ("second"); the terms are not indicative of an order, for example, as to how the functional portions are positioned in an AAV vector of the invention or as to how the functional portions are selected or manipulated or the like.

It should be recognized that reference to a "functional portion" of an AAV nucleic acid molecule as defined above is to be distinguished from reference to a "portion" of an AAV nucleic acid sequence or an AAV vector genome or AAV viral genome. In this regard, it is well recognized in the field of virology that, upon integration of an AAV nucleic acid molecule into a host cell genome, the entire nucleic acid molecule generally does not integrate, but only a portion integrates into the host cell genome. For example, where an AAV vector genome enters a cell and integrates into a host cell chromosome, the entire vector genome generally does not integrate into the chromosome, but only a portion of the vector genome integrates. Thus, reference is made herein to the presence of a "portion" of an AAV nucleic acid molecule, such as an AAV vector genome or an AAV vector plasmid or AAV helper plasmid, in a host cell genome or in a cell or progeny cells thereof.

An AAV ITR provides a useful component of an AAV vector of the invention. AAV2 based vectors containing AAV2 ITR's have been constructed (Srivastava, U.S. Pat. No. 5,252,479, issued Oct. 12, 1993; Carter, U.S. Pat. No. 5,587,308, issued Dec. 24, 1996; each of which is incorporated herein by reference; see, also, Flotte et al., supra, 1993; Koeberl et al., supra, 1997). As disclosed herein, an AAV3 ITR or an AAV6 ITR can be substituted for the AAV2 ITR's of previously described AAV vectors to produce an AAV vector of the invention. An AAV3B or AAV6 ITR, for example, can be obtained by restriction endonuclease digestion of the nucleic acid molecule of SEQ ID NO: 1 or SEQ ID NO: 2, respectively, or can be synthesized using routine chemical or enzymatic methods. Although an entire ITR can be used in a viral vector of the invention, routine methods such as deletion analysis can be used to identify a minimum ITR sequence that allows for packaging and replication of an AAV vector genome containing the ITR sequence. In addition, where the host cell expresses an AAV Rep protein, the sequences of an ITR in an AAV vector genome that direct stable integration of the vector genome into the host cell genome can be determined. In this regard, it should be recognized that an AAV vector plasmid and an AAV vector genome, upon introduction into a cell, can randomly integrate into the cell genome. In addition, where a host cell expresses AAV Rep, the AAV vector genome of an AAV viral vector can stably integrate into chromosome 19.

In general, AAV viral vectors provide significant advantages over other vectors, including other viral vectors. For example, an AAV viral vector comprising only the ITR's of AAV3B or AAV6, but excluding other AAV nucleic acid sequences, can integrate into a genome of a cell expressing the AAV Rep protein, such that a heterologous nucleic acid sequence contained in the vector is stably maintained in the cell. In addition, AAV viral vectors can be produced at a high titer and the AAV viral particle is stable, for example, to relatively high temperatures. Furthermore, the identification of additional AAV isolates and serotypes, as disclosed herein, provides the ability to construct AAV viral vectors that have a desired host range, for example, by generating hybrid AAV virions containing an AAV viral genome having ITR's of one serotype and one or more capsid proteins, or functional portions thereof, of a different serotype.

An AAV viral vector of the invention can be constructed such that, even if adenoviral infection of a cell containing the vector occurs, the AAV nucleic acid sequence is defective for replication, packaging or the like. Such an AAV viral vector can lack AAV nucleic acid sequences encoding, for example, a Rep protein, which then must be provided in trans in order to produce AAV virions. Other advantages provided by AAV vectors is that the AAV vectors target the nucleus. In addition, AAV can infect quiescent cells. Furthermore, increased transduction efficiency of AAV viral vectors can be effected by stimulating DNA repair in a cell to be targeted (Russell et al., Proc. Natl. Acad. Sci., USA 92:5719–5723 (1995), which is incorporated herein by reference).

AAV2 viral vectors have been constructed and used to transfer genes into a wide variety of mammalian cells. AAV2 viral vectors transduce cells in several organs, including brain, muscle, lung and liver, when delivered in vivo (Alexander et al., supra, 1996; Fisher et al., supra, 1996; Flotte et al., supra, 1993; Xiao et al., supra, 1996). However, wide variability in transduction efficiencies occur among different cell types, poor in vivo transduction rates occur following vector readministration, a large number of viral particles is required for effective transduction of certain cell types, and some viral infections lead only to transient gene expression.

An AAV viral vector of the invention provides a means to increase transduction efficiency of a particular host cell because the AAV virion containing the AAV vector genome can be modified to express a capsid protein of an AAV serotype that preferentially transduces the selected host cell. AAV3B and AAV6 viral vectors were prepared and compared with AAV2 viral vectors for the ability to transduce various cell types was compared (see Example III). The AAV viral vectors transduced BHK21 hamster cells, HT1080 human osteosarcoma cells, 293 human kidney cells, K562 human myeloid leukemia cells, COS1 monkey cells and, except for AAV6, CHO K1 cells (see FIG. 5). In addition, the transduction efficiency of the viral vectors varied with respect to the various cell lines tested. These results indicate that the AAV3B and AAV6 infectious clones can be used to construct AAV viral vectors and that viral vectors based, at least in part, on a particular AAV serotype can be used to transduce specific host cells at different rates. In particular, the transduction efficiency of a selected host cell can be increased by constructing AAV viral vectors, which can be hybrid AAV vectors, having capsid proteins of an AAV serotype that preferentially transduces the cells.

The AAV3B and AAV6 viral vectors of the invention provide additional advantages over the current AAV2 vectors. In particular, a limitation of using AAV2 vectors is that many adults have neutralizing antibodies against AAV2 (Muzyczka, supra, 1992). Although the effects of these antibodies on in vivo gene transfer using AAV have not been studied in humans, the presence of high titer neutralizing antibodies to AAV2, which likely will decrease AAV2 infectivity of human individuals. In this regard, additional transduction events are not observed after readministration of AAV2 vectors in mice, suggesting that the host immune response can completely prevent transduction (Xiao et al., supra, 1996).

The present invention provides a means to identify the presence of neutralizing antibodies to an AAV serotype and, based on this information allows the selection of an AAV viral vector, to which an individual previously has not been exposed or to which a minimal antibody response has been induced, or allows the selection of a hybrid AAV virion, which presents epitopes to which the individual previously has not been exposed or has not developed antibodies. Thus, prior to administering an AAV viral vector to a vertebrate, which can be a human or other mammal, the vertebrate first can be examined for the presence of neutralizing antibodies to AAV2, AAV3A, AAV3B or AAV6. Where neutralizing antibodies against AAV2, for example, are detected, an AAV vector genome contained within a viral particle comprising non-AAV2 capsid proteins can be administered to the individual, thereby avoiding the neutralizing AAV2 antibodies. Alternatively, an AAV viral vector containing a hybrid capsid protein can be used, for example, where the AAV2 capsid protein epitopes recognized by neutralizing antibodies are replaced with the corresponding portions of an AAV3B or an AAV6 capsid protein. Such an AAV viral vector can be administered, for example, for a gene therapy procedure or to produce a transgenic non-human mammal.

Although not necessarily so, an AAV viral vector or an AAV vector plasmid of the invention generally is an expression vector, wherein a heterologous nucleic acid sequence contained in the vector is expressed. Accordingly, a heterologous nucleic acid molecule is operably linked to a promoter and, if desired, to an enhancer, either of which can confer constitutive or inducible expression or can confer tissue specific expression of the heterologous nucleic acid sequence. Regulatory elements are well known in the art and include, for example, promoters such as the metallothionein, which is constitutively expressed in most cell types and also is inducible; the myoD promoter, which is expressed in muscle cells; the lck promoter, which is expressed in T cells; the myelin basic protein promoter, which is expressed in glial cells; and the dopamine β-hydroxylase promoter or the preproenkephalin promoter, which are expressed in particular neuronal cells; and enhancers such as the SV40, cytomegalovirus and Rous sarcoma virus enhancers. Other regulatory elements, to which a heterologous nucleic acid sequence can be operably linked, include a polyadenylation signal, a ribosome binding sequence or a consensus splice acceptor or splice donor site, if required.

As used herein, the term "operably linked," when used in reference to a regulatory element and a heterologous nucleic acid molecule, means that the regulatory element is positioned with respect to the heterologous nucleic acid sequence such that the element exhibits its regulatory activity with respect to the heterologous nucleic acid sequence. For example, a promoter element can contain a TATAA sequence, which generally is positioned approximately 30 nucleotides upstream of a transcribed nucleic acid sequence, whereas a polyadenylation signal is positioned downstream of the sequence to be transcribed. In comparison, an enhancer or a silencer generally can be positioned hundreds of nucleotides upstream or downstream of the transcribed nucleic acid sequence without substantially affecting its regulatory activity.

A regulatory element useful in an AAV viral vector or vector plasmid of the invention can be a regulatory element that normally is associated with the heterologous nucleic acid sequence in a cell or can be a regulatory element that normally is present in an AAV serotype or, if desired, can be heterologous to both AAV and the organism from which the heterologous nucleic acid sequence to be expressed was obtained. For example, where the heterologous nucleic acid sequence to be expressed by the AAV vector is a cloned cDNA sequence encoding a polypeptide, the RNA from which the cDNA was prepared generally contains a ribosome binding site and a polyadenylation signal and, therefore, the cDNA encodes these regulatory elements. However, one or both of these regulatory elements, as well as any other such element, can be deleted and substituted with a corresponding, but heterologous regulatory element, which can be a component of the AAV vector or can be operably linked to the heterologous nucleic acid molecule.

The p6 promoter of wild type parvovirus B19 is an example of a promoter that can be operably linked to a heterologous nucleic acid molecule in a vector of the invention (Srivastava, supra, 1993). The B19 p6 promoter has a limited host range and exhibits tissue tropism for the erythroid elements of bone marrow, thus providing a means to express a heterologous nucleic acid sequence specifically in erythroid precursor cells. The p6 promoter is present within nucleotides 200 to 424, including a consensus TATATATA sequence beginning at nucleotide 320 in B19 (Shade et al., J. Virol. 58:921–936 (1986), which is incorporated herein by reference). The promoter sequence can be obtained by restriction endonuclease digestion of B19 or of a B19 derived plasmid such as pYT103 and pYT107 (Cotmore et al., Science 226:1161–1165 (1984), which is incorporated herein by reference) or can be chemically synthesized using routine methods.

Where the heterologous nucleic acid sequence in an AAV viral vector or vector plasmid of the invention encodes a polypeptide, the nucleic acid sequence either contains the translation initiation and termination signals normally associated with the sequence in nature, or such regulatory elements are operably linked to the heterologous nucleic acid sequence. It can be useful, for example, to operably link a nucleic acid sequence encoding a secretory signal peptide, a mitochondrial localization signal peptide, a nuclear localization signal peptide or the like to the heterologous nucleic acid sequence, so as to direct the encoded polypeptide extracellularly or to a particular cellular compartment, as desired.

A nucleic acid sequence encoding a specific tag such as the FLAG peptide or a His-6 peptide also can be operably linked to the heterologous nucleic acid sequence such that, upon expression of an encoded polypeptide, detection of the tag can facilitate identification or purification of the encoded polypeptide. In addition, a heterologous nucleic acid sequence can comprise a recombinant molecule encoding a first polypeptide operably linked to a second polypeptide, such that the coding sequences are in frame with respect to each other and, upon expression, a fusion protein is produced. Fusion proteins comprising an antigen binding portion of an antibody can be particularly useful, for example, to target the fusion protein to a cell expressing a particular antigen.

The various AAV3B and AAV6 nucleic acid sequences useful for constructing an AAV viral vector or an AAV vector plasmid or helper plasmid of the invention can be modified, for example, by ligation of appropriate restriction endonuclease linker or adapter sequences. The availability of such AAV sequences, which provides a convenient means for constructing a vector or plasmid, as desired, and for inserting into the vector or plasmid the appropriate regulatory elements or, if appropriate, heterologous nucleic acid sequences or the like, which can contain complementary restriction sites to facilitate operably linking the sequences into the vector. In particular, the AAV3B and AAV6 nucleic acid sequences can be modified such that they can be substituted conveniently into previously described AAV2 vectors (see Example III; see, also, Srivastava, supra, 1993; Carter, supra, 1996; Flotte et al., supra, 1993; Koeberl et al., supra, 1997).

Methods for constructing AAV3B or AAV6 vector plasmid or AAV helper plasmid constructs are routine and well known to those in the art (see Example III; see, also, Sambrook et al., "Molecular Cloning: A Laboratory Manual" (Cold Spring Harbor Laboratory Press 1989), which is incorporated herein by reference). The order of the ligation of the various components of an AAV3B or AAV6 vector containing a heterologous nucleic acid sequence can be varied as desired. However, where the AAV vector, itself, does not contain the requisite regulatory elements, it can be particularly convenient first to operably link the heterologous nucleic acid molecule to the regulatory elements, then to insert this cassette into the appropriate site in the AAV vector. Insertion of such a cassette is facilitated if the AAV vector plasmid is constructed to contain a multiple cloning site at an appropriate position, for example, between the ITR's or upstream or downstream of a regulatory element contained in the vector.

The invention further provides vertebrate cells, including mammalian cells, containing an AAV3B or AAV6 nucleic acid molecule, or functional portion thereof, or an AAV vector genome or a portion of an AAV vector genome, as well as the progeny of such cells. The cells can be transfected or transduced in vitro and maintained in vitro; can be transfected or transduced in vitro and administered to a mammal; or can be transfected or transduced in vivo by administration of the vector to the mammal. Such cells, which contain AAV3B or AAV6 nucleic acid sequences, are referred to generally herein as "host cells." In addition, cells that arise by the division of host cells are referred to herein as "progeny cells."

Vertebrate cells can be transfected with a plasmid containing AAV nucleic acid sequences, for example, an AAV vector plasmid or an AAV helper plasmid, or can be transduced with an AAV viral vector, which contains an AAV vector genome, to produce a host cell. For example, an AAV viral vector can be used to transduce a vertebrate cell with the vector genome contained within the viral vector. Generally, the AAV vector genome integrates into the host cell genome or is maintained episomally. In both cases, mitosis of the host cell produces progeny cells. However, in the former case, all of the progeny cells contain the integrated vector genome, whereas, in the latter case, only a fraction of the cells contain the vector genome and, therefore, are host cells. Progeny cells containing a stably integrated AAV vector genome are particularly useful, for example, as a source of the product of a heterologous nucleic acid molecule contained in the vector genome.

Host cells or progeny cells can be used in vitro, for example, to maintain a particular AAV nucleic acid molecule, which can contain a heterologous nucleic acid sequence and, therefore, can express a particular polypeptide or therapeutic RNA. Such cells be used as a source of a polypeptide or an RNA molecule encoded by the heterologous nucleic acid sequence such that the polypeptide or RNA molecule can be obtained in a substantially purified form, if desired. Such host cells or the progeny cells thereof also can be introduced into a subject, particularly where the cells originally were obtained from the subject, such that the cells can provide the subject with an expressed polypeptide, for example, thereby providing a means of ex vivo gene therapy. In addition, a host cell that is stably transfected with an AAV helper plasmid can be used as a helper cell to produce AAV viral vectors containing an AAV vector genome.

An AAV3B or AAV6 nucleic acid molecule, including an AAV infectious clone or vector genome or an AAV vector plasmid or helper plasmid, can be introduced into a mammalian cell by transfection, microinjection, electroporation, particle injection, lipofection or any other such method routine in the art for introducing a nucleic acid molecule into a cell. In addition, an AAV viral vector containing an AAV vector genome can be introduced into a cell by transduction. As used herein, the term "transduction" refers to viral particle mediated introduction of a heterologous nucleic acid molecule into the cell. In the case of AAV, such viral particle entry into a cell likely is due to a receptor mediated mechanism. However, if desired, an AAV virion can be encapsulated, for example, in a liposome, which can be used as a means to introduce the virion into a cell. It is recognized that, upon entering a cell, an AAV nucleic acid molecule can be maintained episomally or can be integrated into the cellular genome. Routine methods such as Southern blot analysis or passaging of the cells can be used to distinguish between an episomal and an integrated AAV nucleic acid sequence.

AAV viral vectors containing an AAV vector genome can be produced by cotransfecting helper virus infected cells with an AAV vector plasmid (or an AAV viral vector) and an AAV helper plasmid. For example, an AAV vector genome can be packaged into mature AAV3B or AAV6 viral particles by cotransfecting adenovirus-infected cells with the AAV vector plasmid and with a helper plasmid, which encodes AAV3B or AAV6 Rep and Cap proteins. Following cotransfection, AAV virions are isolated, for example, by cesium chloride gradient centrifugation and heating at 56° C. for one hour to inactivate any contaminating adenovirus. The resulting AAV viral vectors, which contain the AAV vector genome, can be used to transduce host cells (see Example III).

A host cell of the invention or progeny cells thereof can be used as a source of AAV3B or AAV6 viral particle production or AAV3B or AAV6 polypeptide production. Accordingly, the invention also provides substantially purified AAV3B or AAV6 polypeptides, which are encoded by a portion of SEQ ID NO: 1 or SEQ ID NO: 2, respectively. In particular, a substantially purified polypeptide of the invention, which can be a Rep protein or a capsid protein of AAV3B or AAV6 (see FIG. 1), is characterized in that it has an amino acid sequence that is different from the amino acid sequence of the corresponding polypeptide encoded by AAV2 or AAV3A. As used herein, the term "corresponding polypeptide," when used in reference to an AAV polypeptide, means a polypeptide in one AAV serotype or AAV isolate that serves the same general function as a polypeptide in a different AAV serotype or AAV isolate. For example, AAV3A VP1 and AAV3B VP1 are corresponding polypeptides, as are AAV2 Rep78 and AAV6 Rep78.

A substantially purified polypeptide of the invention is exemplified by the AAV3B viral capsid proteins, VP1, VP2 and VP3 (SEQ ID NO: 6), which differ from the corresponding AAV3A capsid proteins (SEQ ID NO: 5) at amino acid positions 144, 145, 321 and 322 (see FIG. 2). A polypeptide of the invention also is exemplified by the AAV6 viral capsid proteins (SEQ ID NO: 7) and by the AAV3B and AAV6 Rep proteins (FIG. 3; SEQ ID NOS: 10 and 11, respectively).

The invention also provides peptide portions of the AAV polypeptides of the invention. As used herein, the term "peptide portion" means a contiguous amino acid sequence of an AAV3B or an AAV6 polypeptide, provided the peptide is not contained within a different AAV serotype or isolate. In general, a peptide portion of an AAV polypeptide of the invention is at least six amino acids in length, although peptide portions of about 10 amino acids or 20 amino acids in length can be particularly useful, for example, as immunogens to raise antibodies specific for a particular polypeptide of a specific AAV serotype or isolate. A peptide portion of an AAV polypeptide is exemplified by amino acids 142 to 147 of AAV3B VP1 (SEQ ID NO: 6; FIG. 2), since this six amino acid sequence is unique to AAV3B as compared to AAV2, AAV3A and AAV6. Similarly, inspection of FIG. 3 or a computer search of the amino acid sequences encoded by the AAV2 (SEQ ID NO: 3), AAV3A (Muramatsu et al., supra, 1996), AAV3B (SEQ ID NO: 1) and AAV6 (SEQ ID NO: 2) genomic nucleic acid sequences can be used to identify such unique peptide portions of an AAV3B or an AAV6 polypeptide.

As used herein, the term "substantially purified," when used in reference to an AAV polypeptide, means that the polypeptide is present in a form that is at least two fold enriched as compared to the relative concentration in which the polypeptide is found in nature. Generally a substantially purified AAV3B or AAV6 polypeptide of the invention is at least ten fold enriched and, in particular, the polypeptide is about 90% free of contaminating viral or host cell material, as determined, for example, by SDS-PAGE and silver staining. It is noted that the term "substantially purified" is used similarly herein in reference to an antibody of the invention (see below). A substantially purified antibody of the invention can be obtained, for example, by isolating the serum fraction of a blood sample from an individual exposed to an appropriate AAV immunogen.

AAV3B and AAV6 polypeptides generally exist in association with the AAV viral particle in a host cell or are expressed from an AAV nucleic acid sequence in a cell. Where the polypeptide is associated with a viral particle in a cell, substantially purified AAV3B and AAV6 polypeptides can be obtained in the form of the viral particle by cesium chloride density gradient centrifugation and isolation of the fraction containing the AAV virions. Such a method can be particularly useful for obtaining isolated AAV3B or AAV6 viral particles from a cell containing a helper adenovirus, since adenovirus viral particles have a density that is different from the density of AAV virions.

AAV3B or AAV6 polypeptides can be substantially purified from an isolated viral particle by disrupting the structure of the virus using, for example, a detergent such as sodium dodecyl sulfate, then fractionating the polypeptides by chromatography, electrophoresis or other such method (see, for example, Davison and Elliott, "Molecular Virology: A practical approach" (IRL Press, 1993), which is incorporated herein by reference). The use of antibodies that specifically bind AAV3B or AAV6 polypeptides can facilitate obtaining the polypeptides in a substantially purified form, for example, by linking the antibodies to a solid matrix and purifying the polypeptides by affinity chromatography. Such a method also can be useful for purifying, for example, a Rep protein that is expressed from a viral nucleic acid sequence in a host cell.

A substantially purified AAV3B or AAV6 polypeptide, or a peptide portion thereof, also can be obtained by expressing a portion of an AAV3B or AAV6 nucleic acid molecule that encodes the particular polypeptide. For example, AAV3B Rep78 can be obtained by expressing nucleotides 318 to 2192 of SEQ ID NO: 1, whereas AAV6 Rep78 can be obtained by expressing nucleotides 320 to 2191 of SEQ ID NO: 2 (see FIG. 1). Similarly, in view of the disclosure of SEQ ID NOS: 1 and 2 (FIG. 1), nucleotide sequences encoding the various other AAV3B or AAV6 polypeptides can be identified such that the skilled artisan can obtain a nucleic acid sequence encoding a desired AAV3B or AAV6 polypeptide or peptide portion thereof, clone the sequence into an appropriate expression vector, and express the polypeptide in an appropriate host cell such that the polypeptide can be obtained in a substantially purified form. For purposes of expressing an AAV polypeptide, an appropriate expression vector can be, for example, baculovirus vector, which conveniently produces large amounts of a polypeptide, or can be a bacterial cell or mammalian cell expression vector. Methods for purifying polypeptides are well known in the art (see, for example, Deutscher, "Guide to Protein Purification," in Meth. Enzymol. vol. 182 (Academic Press 1990), which is incorporated herein by reference).

The present invention also provides substantially purified antibodies that specifically bind to an AAV3B or an AAV6 polypeptide. As used herein, the term "antibody" is used in its broadest sense to include polyclonal and monoclonal antibodies, as well as antigen binding fragments of such antibodies. With regard to an antibody of the invention, which is specific for an AAV3B or AAV6 polypeptide of the invention, the term "antigen" is used herein to mean an AAV3B or an AAV6 polypeptide of the invention or a peptide portion thereof comprising an epitope that is unique for AAV3B or AAV6, respectively. An antibody of the invention, or an antigen binding fragment thereof, is characterized in that it specifically bind to an epitope of an AAV3B or an AAV6 polypeptide with an affinity of at least about $1 \times 10^5$ $M^{-1}$ and, generally, at least about $1 \times 10^6$ $M^{-1}$. Fab, F(ab')$_2$, Fd and Fv fragments of such an antibody are examples of antigen binding fragments of an antibody that retain specific binding activity for the AAV3B or AAV6 polypeptide and, therefore, are included within the definition of an antibody.

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275–1281 (1989), which is incorporated herein by reference). These and other methods of making, for example, chimeric, humanized, CDR-grafted, single chain, and bifunctional antibodies are well known to those skilled in the art (Hoogenboom et al., U.S. Pat. No. 5,564,332, issued October 15, 1996; Winter and Harris, *Immunol. Today* 14:243–246 (1993); Ward et al., *Nature* 341:544–546 (1989); Harlow and Lane, "Antibodies: A laboratory manual" (Cold Spring Harbor Laboratory Press, 1988); Hilyard et al., "Protein Engineering: A practical approach" (IRL Press 1992); Borrabeck, "Antibody Engineering" 2d ed. (Oxford University Press 1995); each of which is incorporated herein by reference).

An antibody of the invention can be raised using as an immunogen a substantially purified AAV3B or AAV6 polypeptide, which can be substantially purified from an isolated AAV3B or AAV6 virion, respectively, or can be produced recombinantly, or can be a peptide portion of an AAV3B or AAV6 polypeptide, which can be chemically synthesized. Particularly useful peptide portions of an AAV polypeptide are those portions that comprise an epitope present in the native AAV polypeptide. A non-immunogenic peptide portion of an AAV3B or AAV6 polypeptide can be made immunogenic by coupling the hapten to a carrier molecule such bovine serum albumin (BSA) or keyhole limpet hemocyanin (KLH), or by expressing the peptide portion as a fusion protein such as a glutathione-S-transferase (GST) fusion protein, which can be expressed readily from a commercially available vector. Such a fusion protein can be particularly useful because the GST component of the fusion protein readily binds to glutathione, which can be attached to an insoluble matrix, thereby providing a simple affinity chromatography method of purifying the immunogen. Various other carrier molecules and methods for coupling a hapten to a carrier molecule are well known in the art (see Harlow and Lane, supra, 1988; see, also, Hermanson, "Bioconjugate Techniques" (Academic Press 1996), which is incorporated herein by reference).

Particularly useful antibodies of the invention are those that specifically bind to an AAV6 polypeptide but not to the corresponding polypeptide of a different AAV serotype. Similarly, an antibody that specifically binds to an AAV3B polypeptide, but not to the corresponding AAV3A polypeptide, or to the corresponding polypeptide of a different AAV serotype is useful. An antibody that specifically binds to an epitope comprising amino acids 142 to 147 or amino acids 320 to 325 of AAV3B VP1 (SEQ ID NO: 6) is an example of an antibody of the invention, since such epitopes are unique to AAV3B. It should be recognized, however, that an antibody that binds to both an AAV3B polypeptide and the corresponding polypeptide in AAV3A also can be useful, for example, to identify the presence of an AAV3 serotype infection in an individual.

It is further recognized that an antibody of the invention, particularly a monoclonal antibody, can be used as an immunogen to raise anti-idiotypic antibodies, which mimic the epitope of the AAV polypeptide or peptide portion thereof used to stimulate production of the original antibody. An anti-idiotypic antibody can be used as a substitute for the polypeptide that is mimicked and provides the advantage that a hybridoma cell line producing the anti-idiotypic antibody provides a continual source of the antibody. For example, an anti-idiotypic antibody that mimics a unique epitope of AAV3B VP1 can be used as an "antigen" to identify the presence of antibodies against AAV3B in an individual.

An antibody that specifically binds an AAV3B or an AAV6 polypeptide is useful for determining the presence or level of an AAV3B or an AAV6 polypeptide, respectively, in a tissue sample, which can be, for example, a blood sample, a lysate or a histological section. The identification of the presence or level of such a polypeptide in the sample can be made using well known immunoassay and immunohistochemical methods (Harlow and Lane, supra, 1988).

A protein such as a substantially purified AAV polypeptide or antibody of the invention can be labeled so as to be detectable using methods well known in the art (Hermanson, supra, 1996; Harlow and Lane, supra, 1988). For example, the protein can be labeled with various detectable moieties including a radiolabel, an enzyme, biotin or a fluorochrome. Reagents for labeling a protein such as an antibody of the invention can be included in a kit containing the antibody or can be purchased separately from a commercial source.

Following contact, for example, of a labeled antibody with a sample such as a tissue homogenate or a histological section of a tissue, specifically bound labeled antibody can be identified by detecting the particular moiety Alternatively, a labeled second antibody can be used to identify specific binding of an unlabeled antibody that specifically binds an AAV3B or an AAV6 polypeptide. A second antibody generally will be specific for the particular class of the first antibody. For example, if the antibody that specifically binds the AAV polypeptide is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody, which specifically binds the AAV polypeptide, then the sample is contacted with the labeled second antibody, which specifically binds to the first antibody and results in a labeled sample.

Methods for raising polyclonal antibodies, for example, in a rabbit, goat, mouse or other mammal, and methods for substantially purifying such antibodies are well known in the art. In addition, monoclonal antibodies can be obtained using methods that are well known and routine in the art (Harlow and Lane, supra, 1988). Essentially, spleen cells, for example, from a mouse immunized with a substantially purified AAV3B or AAV6 polypeptide of the invention are fused to an appropriate myeloma cell line such as SP/02 myeloma cells to produce hybridoma cells. Cloned hybridoma cell lines can be screened using a labeled AAV polypeptide, as appropriate, to identify clones that secrete the desired monoclonal antibodies. Those hybridomas having a desirable specificity and affinity can be isolated and utilized as a continuous source of the antibodies, which are useful, for example, for preparing standardized kits containing the antibody. Similarly, a recombinant phage that expresses, for example, a single chain antibody that specifically binds an AAV3B or AAV6 polypeptide also provide a monoclonal antibody that can used for preparing standardized kits.

The present invention also provides AAV3B or AAV6 nucleotide sequences, which can be useful for identifying the presence of AAV3B or AAV6 in a sample. Such nucleotide sequences of the invention generally comprise at least nine contiguous nucleotides of SEQ ID NO: 1 or SEQ ID NO: 2 and can be used as PCR primers or as hybridization probes, for example, to identify a mammalian cell containing AAV3B, AAV6 or a functional portion thereof, including an AAV3B or AAV6 vector. In addition, a nucleotide sequence of the invention can comprise nucleotide positions 425 and 426, or nucleotides 2638 to 2641, or nucleotides 3170 to 3173 of AAV3B, which can be useful, for example, for distinguishing an AAV3B viral genome from an AAV3A viral genome (see Table 1). If desired, a nucleotide sequence of the invention can be detectably labeled with any of various moieties, including a radionuclide, a fluorochrome, a luminescent marker or a ferromagnetic substance, using routine methods and commercially available kits.

A nucleotide sequence of the invention is characterized, in part, by the ability to hybridize under stringent conditions to an AAV3B or an AAV6 nucleic acid molecule (SEQ ID NOS: 1 and 2, respectively). Appropriately stringent hybridization conditions will depend, for example, on the relative G:C content of the nucleotide sequence and the length of the sequence and can be determined empirically or can be estimated using well known formulas (see, for example, Sambrook et al., supra, 1989). In particular, stringent conditions are selected such that a nucleotide sequence of the invention hybridizes to one of the nucleic acid molecules shown as SEQ ID NO: 1 or SEQ ID NO: 2 or SEQ ID NO: 3 or the sequence of the AAV3A viral genome (Muramatsu et al., supra, 1996), but not to the others.

As a result of the high degree of sequence identity shared between AAV3B and AAV3A, the skilled artisan would recognize that a select few sequences of AAV3B have the characteristics required of a nucleotide sequence of the invention. Such sequences can be identified by visual inspection of SEQ ID NO: 1 as compared to the sequence of the AAV3A viral genome (Muramatsu et al., supra, 1996) or, more conveniently, by performing a computerized search of the sequences to identify nonhomologous sequences, then by examining the specificity using routine hybridization methods. In particular, as discussed above, a nucleotide sequence comprising about 14 to 18 nucleotides, including nucleotide positions 425 and 426, or nucleotides 2638 to 2641, or nucleotides 3170 to 3173 of AAV3B can be useful for distinguishing an AAV3B viral genome from an AAV3A viral genome because such AAV3B nucleotide sequences are sufficiently mismatched with respect to the corresponding sequences in AAV3A that they will not hybridize to an AAV3A viral genome under stringent hybridization conditions (see Table 1).

The invention also provides methods of treating a pathologic condition in a vertebrate, particularly a mammal, comprising contacting the cells of the vertebrate with an AAV viral vector or an AAV vector plasmid containing a heterologous nucleic acid sequence, wherein expression of the heterologous nucleic acid sequence provides a therapeutic benefit to the vertebrate cells, specifically, or to the vertebrate, generally. Thus, the invention provides methods for treating pathologic conditions in mammals, particularly humans, including pathologies such as cystic fibrosis, cancer, AIDS, atherosclerosis, sickle cell anemia, thalassemias, clotting deficiencies, diabetes, and autosomal recessive disorders where the gene involved in the disorder is known. A mammal to be treated by such a method can be any mammal that suffers from such diseases, including, for example, humans or other primates, domestic animals such as dogs or cats, farm animals such as cattle, sheep, horses, or the like, or rodents such as mice or rats, which often are used as experimental models for investigating such diseases. Thus, an AAV viral vector or an AAV vector plasmid of the invention is particularly useful as a medicament for treating a mammal such as a human.

It is recognized that a mammal transduced with an AAV viral vector or an AAV vector plasmid of the invention containing a heterologous nucleic acid sequence can provide a unique model system that is useful, for example, for examining the effect of expressing the heterologous nucleic acid sequence in an individual. Such a mammal also can provide a source for production of a polypeptide or an RNA expressed from the heterologous nucleic acid sequence. Accordingly, the present invention provides transgenic mammals, which are not humans, having stably integrated into their genomic DNA an AAV nucleic acid molecule such as an AAV vector genome containing a heterologous nucleic acid sequence.

A polypeptide encoded by an AAV vector of the invention can provide a biological function that aids in treatment of a pathologic condition. As used herein, the term "treat" or "treatment," when used in reference to a pathologic condition, means that the severity of the conditioned is lessened as determined using clinical criteria generally used to characterize the disease. For example, where the pathologic condition is cystic fibrosis, effective treatment of the condition can be identified by detecting a measurable decrease in electrolytes in a sample of sweat obtained from the patient or by detecting an improved ventilatory capacity in the patient. Where the pathologic condition is cancer, effective treatment of the condition can be identified by detecting, for example, a decreased growth rate of a tumor or a decrease in the tumor size using a diagnostic imaging method.

An encoded polypeptide can be expressed in a cell in order to replace a corresponding, but defective polypeptide in the cell. For example, the polypeptide can be the cystic fibrosis transmembrane conductance regulator (CFTR), the expression of which replaces the loss of chloride ion reabsorption that occurs due to expression of a defective CFTR by the cystic fibrosis patient. Similarly, the polypeptide can be a normal tumor suppressor such as p53, the expression of which replaces a defective p53 protein expressed in a patient having, for example, colorectal cancer. In addition, expression, for example, of a normal retinoblastoma protein in the retinal cells of a child predisposed to retinoblastoma can provide a preventative treatment. The encoded polypeptide may be a complete protein, or may be the active or an immunogenic part of the protein.

Where the pathologic condition to be treated is due to a genetic defect such as a mutation, the skilled artisan will know the particular heterologous nucleic acid sequence to be incorporated into a vector of the invention. However, the artisan also will recognize that a therapeutic benefit can be obtained in treating various non-genetic pathologies by expressing, for example, a hematopoietic growth factor such as granulocyte-macrophage colony stimulating factor, macrophage colony stimulating factor, granulocyte colony stimulating factor or erythropoietin; a cytokine such as tumor necrosis factor, mast cell growth factor, or one or more of interleukins 1–16, in a cell, wherein the expression can increase, for example, the immunoresponsiveness of the individual.

An encoded polypeptide also can provide a cell or a mammal containing the cell with a therapeutic advantage by allowing the cell to survive (or die) upon exposure to a particular agent. For example, the selectable polypeptide can be herpes virus thymidine kinase (HSV TK), which, upon expression in a cell, renders the cell susceptible to killing by a drug such as gancyclovir. Thus, introduction of a nucleic acid sequence encoding HSV TK into a population of cells, such as tumor cells, followed by exposure of the cells to gancyclovir, results in death of the cells expressing HSV TK, but not of cells not expressing the polypeptide. It is recognized, however, that the presence of certain heterologous nucleic acid sequences in an AAV vector can inhibit AAV DNA replication (see Muzyczka, supra, 1992). Routine methods are used, therefore, to confirm that the insertion of a particular heterologous nucleic acid sequence into an AAV vector is compatible with AAV functions, as appropriate.

An encoded polypeptide also can be, for example, aminoglycoside transferase such as neomycin phosphotransferase, which confers G418 resistance ($G418^R$) upon a cell and allows cells expressing The polypeptide to survive upon exposure to G418 whereas other cells are killed. Expression of such a polypeptide can provide a means to select the particular population of cells containing the AAV vector from which The polypeptide is expressed. Similarly, expression of adenine phosphoribosyl transferase (APRT) allows selection of APRT-deficient cells that have incorporated an AAV vector, from which APRT is expressed.

A heterologous nucleic acid sequence also can encode a polypeptide that is conveniently detectable. Such a detectable polypeptide can be, for example, an enzyme such as luciferase, β-galactosidase, alkaline phosphatase or the like, which, when expressed in a cell, allows identification of the cell following contact with an appropriate substrate, or a polypeptide such as the green fluorescent protein. The expression of such a polypeptide in cells facilitates identification of cells containing the vector from which the polypeptide is expressed (see Example III). The skilled artisan will recognize that polypeptides such as those encoding a selectable marker or a detectable marker generally are expressed in combination with a second polypeptide, which provides a therapeutic function, or with a therapeutic RNA.

An AAV viral vector or an AAV vector plasmid can be used to introduce a heterologous nucleic acid sequence encoding a therapeutic polypeptide and a nucleic acid molecule encoding a detectable polypeptide into cells in a patient. For example, where the goal is to target expression of the therapeutic polypeptide to specific cells, either by utilizing an AAV viral vector tropic for the cells or by expressing the polypeptide from a tissue specific regulatory element, the vector can be administered to the patient, then a biopsy of the tissue can be obtained and readily examined for expression of the detectable polypeptide, the expression of which indicates that the vector encoding the therapeutic polypeptide is present in the tissue.

A heterologous nucleic acid sequence also can encode a structural or enzymatic RNA molecule such ribosomal RNA, transfer RNA, the RNA component of telomerase, or a therapeutic RNA. As used herein, the term "therapeutic RNA" means an enzymatic or structural RNA molecule, including an antisense RNA molecule, a ribozyme, or a triplex RNA molecule, which produces a therapeutic effect. For example, overexpression of an anti-apoptotic protein such as Bcl-2 is associated with various types of cancer and allows the cancer cells to survive under conditions where the cells otherwise would be killed. In particular, cancer cells that overexpress Bcl-2 are less susceptible to apoptosis induced by chemotherapeutic agents or by radiotherapy. Use of an AAV vector of the invention to introduce, for example, a nucleic acid sequence encoding an antisense Bcl-2 nucleic acid molecule or a ribozyme specific for a Bcl-2 gene transcript can provide a means to reduce the level of Bcl-2 in the cancer cells and, therefore, render the cells more susceptible to chemotherapy or radiotherapy.

The use of an AAV vector of the invention for treating a disease can involve administration of the vector to an individual such that, where the vector is an AAV viral vector, the target cells are transduced by the vector and a heterologous nucleic acid sequence contained in the vector is expressed, or can involve transduction or transfection ex vivo of the cells, which previously have been removed from an individual such as the individual to be treated. Where the vector is introduced into the cells ex vivo, the cells can be expanded in culture, if desired, then implanted or infused into the individual (see, for example, Rosenberg et al., New Engl. J. Med. 323:570–578 (1990); U.S. Pat. No. 5,399,346, issued Mar. 21, 1995, each of which is incorporated herein by reference).

Where an AAV viral vector is introduced into an individual in vivo, the vector can be administered systemically or locally. For example, hepatocytes in rat liver targeted by direct injection or by intravenous injection of AAV viral vectors were transduced to similar levels and expressed human clotting factor IX, which was encoded by the vector (Koeberl et al., supra, 1997). In addition, AAV viral vectors containing a heterologous nucleic acid molecule encoding the CFTR, which is defective in cystic fibrosis patients, were administered directly to the lung using a fiberoptic bronchoscope and CFTR RNA and protein remained detectable in airway epithelium six months after administration (Flotte et al., supra, 1993). AAV viral vectors also have efficiently transduced muscle cells following injection into mouse muscle (Xiao et al., supra, 1996). Furthermore, when AAV viral vectors encoding tyrosine hydroxylase were administered by stereotactic microinjection into rat brain and tyrosine hydroxylase expression persisted for at least four months (Kaplitt et al., *Nat. Genet.* 8:148–154 (1994), which is incorporated herein by reference). These results indicate that AAV viral vectors can be useful for introducing a heterologous nucleic acid sequence into a cell in vivo, such that the product encoded by the heterologous nucleic acid sequence is expressed.

The present invention further provides a method for selecting an AAV viral vector useful for treating an individual by gene therapy, comprising identifying a previous AAV infection in the individual, wherein the presence of a previous infection by an AAV of a particular serotype indicates that an AAV viral vector of a different serotype should be selected to treat the individual. Such a method can utilize, for example, a nucleotide sequence as a hybridization probe to identify the presence of nucleic acids of a particular AAV serotype in a tissue sample obtained from the mammal. A method of the invention also can be performed using antibodies that are specific for a protein expressed by a particular AAV serotype.

A particularly useful method for selecting an AAV viral vector useful for treating an individual by gene therapy utilizes a ligand that is specifically bound by an anti-AAV polypeptide antibody. In this method, a ligand such as an AAV polypeptide, or a peptide portion thereof comprising an epitope, a viral particle, or an anti-idiotypic antibody that mimics an AAV polypeptide, or epitope thereof, is used to identify the presence of antibodies in an individual to be treated by administration of an AAV viral vector. The detection of such antibodies, particularly anti-AAV capsid protein antibodies, which can be neutralizing antibodies, to a particular AAV serotype indicates that the likelihood of infection by an AAV vector of the same AAV serotype is relatively low and, therefore, that a vector comprising a different AAV serotype is preferred for treating the individual.

A viral neutralization or viral vector neutralization assay also can be used to identify the presence of neutralizing antibodies, which can preclude the use of an AAV viral vector of the same serotype as that against which the antibodies are directed. Viral neutralization assays can be performed using well known methods (see, for example, Dimmock, *J. Gen. Virol.* 65:1015 (1984); Dimmock, *Trends Biochem. Sci.* 12:70 (1987), each of which is incorporated herein by reference). For example, an AAV viral vector containing a vector genome comprising a reporter gene encoding alkaline phosphatase or β-galactosidase or the like can be incubated with serum obtained from an individual to be treated. AAV viral vectors that were incubated with the serum and control, untreated viral vectors then can be contacted with appropriate target cells and the transduction efficiency determined by measuring expression of the reporter molecule. A decrease in the transduction efficiency of the AAV viral vectors treated with the individual's serum as compared to the control viral vectors indicates that the individual expresses neutralizing antibody.

As used herein, the term "lignad" means an AAV polypeptide such as an AAV capsid protein of a particular AAV serotype, or an epitope thereof, or an AAV virus, or an anti-idiotypic antibody that mimics an AAV polypeptide or epitope thereof, that is specifically bound by an anti-AAV polypeptide antibody. A method of the invention is performed by obtaining a tissue sample, preferably a blood sample, from the individual to be examined, and contacting the sample with the ligand. In particular, the sample can be contacted with several different ligands representing various AAV serotypes or isolates and various AAV polypeptides. Such a method, which can be, for example, an enzyme linked immunoadsorption assay (ELISA), can be performed under routine conditions for performing such an assay and can include the appropriate controls to confirm the specificity of the assay.

Upon identifying the presence of antibodies in an individual, a virus or viral vector neutralization assay is performed to determine whether the antibodies are neutralizing antibodies, the presence of which can decrease the transduction efficiency of an AAV viral vector. An AAV viral vector for administration to the individual is selected, therefore, by determining that the individual does not express neutralizing antibodies or, where neutralizing antibodies are expressed against all AAV serotypes, by utilizing a hybrid AAV viral vector that lacks the epitopes recognized by the antibodies, or by selecting an AAV viral vector against which the titer of neutralizing antibodies is lowest.

A panel of AAV nucleotide sequences or a panel of antibodies specific for an AAV serotype polypeptide or a panel of anti-AAV polypeptide antibody ligands representative of AAV polypeptides of various AAV serotypes and isolates are particularly useful for screening a sample obtained from a mammal such as a human, such that a suitable AAV viral vector can be selected for introducing a heterologous nucleic acid sequence into the mammal. Thus, the invention provides panels of such AAV nucleotide sequences or of antibodies or of anti-AAV polypeptide antibody ligands. If desired, a panel of such reagents can be in the form of a kit, which can facilitate screening a sample obtained from a mammal.

The following examples are intended to illustrate but not limit the present invention.

EXAMPLE I

Isolation of AAV3B and AAV6

AAV3 and AAV6 viral stocks were grown in adenovirus infected 293 cells and purified from crude lysates of the infected cells. The cells and media were frozen and thawed three times to break the cells, then clarified by centrifugation to remove cellular debris. The virus was concentrated by centrifugation through sucrose. In some cases, the virus isolated from the sucrose gradient was further purified by centrifugation in CsCl. The AAV fraction was dialyzed to remove CsCl and concentrated using Centricon spin columns. AAV DNA was isolated from the purified stocks by digestion with proteinase K, phenol extraction, ethanol precipitation, hybridization to maximize double stranded DNA, and purification of a 4.7 kb band from an agarose gel.

The purified AAV DNA was treated with Klenow polymerase to produce blunt ends, ligated to Xba I linkers, and cloned into the Xba I site of plasmid pACYC184 (Chang and Cohen, *J. Bacteriol.* 134:1141–1156 (1978), which is incorporated herein by reference). This plasmid vehicle uses the p15A replication origin, which replicates at approximately 12–15 copies per *E. coli* chromosome. Using plasmids with lower copy numbers allows propagation of the otherwise unstable inverted terminal repeats, with fewer deletions and rearrangements than occur using higher copy number plasmids.

Several plasmids were isolated and restriction endonuclease analysis indicated that the plasmids contained full length AAV3 and AAV6 viral genomes. In order to confirm that the cloned AAV nucleic acid molecules were infectious, the plasmids were transfected into adenovirus infected 293 cells and AAV virions were purified from cell lysates. The plasmids that produced the most intact, packaged, linear, viral genomes for each were selected and were designated pAAV3B (AAV3B) and pAAV6 (AAV6).

The pAAV3B and pAAV6 infectious clones were used to generate AAV3B and AAV6 viral stocks, respectively. Small scale, crude stocks were prepared by transfecting adenovirus infected 293 cells with pAAV3B or pAAV6, and collecting heat-inactivated cell lysates. Large scale purified stocks were prepared by coinfecting 293 cells with adenovirus and with a crude AAV stock and collecting cell lysates 3 days later. AAV virions were purified from these lysates by treatment with micrococcal nuclease, pelleting through a 40% sucrose cushion and fractionation by CsCl gradient centrifugation.

Fractions collected from the CsCl gradients were examined by refractometry to determine the density of the AAV virions, and the amount of virions present in each fraction was determined by quantitation of intact, single stranded linear genomes by alkaline agarose gel electrophoresis and Southern blot analysis. AAV2 stocks were prepared in a similar manner by using a pAAV2 infectious clone (Laughlin et al., supra, 1983). Virion density peaked at 1.40–1.41 gm/cm$^3$, as expected for AAV. These results confirm that the infectious AAV3B and AAV6 clones support excision, replication and packaging after transfection into adenovirus-infected cells.

EXAMPLE II

Characterization of the AAV3B and AAV6 Infectious Clones

The complete nucleotide sequences of AAV3B and AAV6 were determined for both strands using the dideoxy method. A combination of primer walking and subcloning of subgenomic fragments was used. Sequencing of the terminal repeats required digestion of the viral DNA with restriction endonucleases that had recognition sites within the terminal repeats, then either cloning the desired fragment into a plasmid for sequencing or sequencing it directly from the digested mixture. The full length genomic DNA sequences of AAV3B (SEQ ID NO: 1) and AAV6 (SEQ ID NO: 2) are shown in FIG. 1 and are compared to the corrected sequence of AAV2 (SEQ ID NO: 3). In addition, nucleotide differences between AAV3A (Muramatsu et al., supra, 1996) and AAV3B (SEQ ID NO: 1) are shown in Table 1.

AAV2, AAV3B and AAV6 share 82% to 85% overall sequence homology, which is similar to the 82% homology shared between AAV2 and AAV3A (Muramatsu et al., supra, 1996). In comparison, AAV3B and AAV3A differ at only 17 positions. Although the sequences of important genetic elements are conserved among the three isolates, including the Rep and Cap start codons, the splice donor and acceptor sites of the single intron, the polyadenylation signal, and the secondary structures of the terminal repeats, several differences also are apparent.

Phylogenetic trees were calculated for the capsid proteins (VP1; see FIG. 2) and Rep proteins (Rep78; see FIG. 3)of AAV2, AAV3A, AAV3B and AAV6 using Higgins-Sharp analysis (MacDNASIS; Hitachi Software). The proteins shared similar matching percentages, ranging from 82% to 86%, with AAV6 being slightly more divergent than the others. Several regions of the capsid and Rep proteins have substantial amino acid differences, which are unique to each serotype and may, in part, determine serotype specific interactions. The divergence of AAV6 in the same regions where AAV2 and AAV3 differ indicate that AAV6 is a new AAV serotype.

EXAMPLE III

Construction of AAV Viral Vectors

AAV3B vector plasmids and helper plasmids were constructed from the pAAV3B infectious clone (Example I) by engineering Bgl II restriction sites just upstream of the p5 promoter and downstream of the polyadenylation site (pAAV3Bgl; see FIG. 4; see, also, Russell et al., supra, 1994). The Bgl II fragment containing the rep and cap genes was excised from pAAV3Bgl and inserted into a pBLUESCRIPT (Stratagene; La Jolla Calif.) backbone to create the AAV3B helper plasmid pRepCap3. A cassette containing the human placental alkaline phosphatase gene (AP) under the control of the Moloney murine leukemia virus LTR promoter and the neomycin phosphotransferase gene (neo) under the control of the SV40 early promoter was inserted in place of the rep-cap cassette in pAAV3Bgl to create the AAV3B vector plasmid pA3LAPSN (FIG. 4). A similar strategy was used to produce the AAV6 vector plasmid pA6LAPSN and the helper plasmid pRepCap6.

The AAV3B viral vector, AAV3B-LAPSN, was generated by cotransfecting adenovirus infected 293 cells with pRepCap3 and pA3LAPSN, then collecting cell lysates 3 days later (FIG. 4). AAV3B-LAPSN viral vectors containing the AAV3B vector genome were purified by CsCl gradient centrifugation and heat inactivated to destroy any remaining adenovirus (see Example I). The isolated AAV3B-LAPSN viral vectors contained single stranded linear vector genomes of the expected size as determined by Southern blot analysis. AAV6-LAPSN viral vectors were prepared similarly using pA6LAPSN and pRepCap6.

AAV3B-LAPSN, AAV6-LAPSN and the AAV2 viral vector, AAV2-LAPSN (Russell et al., supra, 1994), were used to transduce BHK21 hamster cells, HT1080 human osteosarcoma cells, 293 human kidney cells, K562 human myeloid leukemia cells COS1 monkey cells and CHO K1 cells. Each AAV viral vector was able to transduce the AP gene, as measured by histochemical staining, and the neo gene, as measured by G418 resistance. The AAV viral vectors transduced each of the different cell lines tested, except with regard to AAV6 on CHO K1 cells (see FIG. 5). In addition, the transduction efficiency of the viral vectors varied with respect to the various cell lines tested. These results indicate that the AAV3B and AAV6 infectious clones can be used to construct AAV viral vectors and that viral vectors based, at least in part, on a particular AAV serotype can be used to efficiently transduce specific host cells at different rates, presumably due to specific receptor interactions.

Although the invention has been described with reference to the example provided above, it should be understood that various changes can be made without departing from the spirit of the invention. Accordingly, the invention is limited only by the claims.

We claim:

1. An isolated adeno-associated virus serotype 6 (AAV6) comprising a genomic nucleic acid sequence as shown in SEQ ID NO: 2 or a nucleic acid sequence complementary to SEQ ID NO: 2.

2. A substantially purified nucleic acid molecule, comprising the nucleotide sequence of SEQ ID NO: 2 or a nucleic acid sequence complementary to SEQ ID NO: 2.

3. An infectious AAV6 clone, comprising a substantially purified double stranded nucleic acid molecule comprising an unique portion of the nucleotide sequence of SEQ ID NO: 2 and a nucleotide sequence complementary thereto.

4. The infectious AAV6 clone of claim 3, which is contained in a plasmid.

5. A cell selected from the group consisting of a host cell containing at least an unique contiguous nucleotide sequence of the infectious clone of claim 3 and a progeny cell produced from said host cell.

6. The infectious clone of claim 4, wherein said plasmid contains a p15A replication origin.

7. An AAV vector genome, comprising a functional portion of a nucleotide sequence of SEQ ID NO: 2 or a sequence complementary to SEQ ID NO: 2, provided said functional portion has a nucleotide sequence that is not present in AAV2 (SEQ ID NO: 3) or in AAV3A (SEQ ID NO: 4).

8. The AAV vector genome of claim 7, wherein said functional portion of SEQ ID NO: 2 is selected from the group consisting of nucleotides 1 to 141 and 4543 to 4683.

9. The AAV vector genome of claim 7, further comprising a heterologous nucleic acid sequence.

10. An AAV viral vector, comprising the AAV vector genome of claim 7.

11. The AAV vector genome of claim 9, wherein said heterologous nucleic acid sequence encodes a polypeptide.

12. The AAV vector genome of claim 9, wherein said heterologous nucleic acid sequence encodes an RNA molecule.

13. The AAV vector genome of claim 12, wherein said RNA molecule is a therapeutic RNA.

14. A cell selected from the group consisting of a host cell transduced by the viral vector of claim 10 and a progeny cell produced from said host cell.

15. An AAV plasmid, comprising a functional portion of a nucleotide sequence of SEQ ID NO: 2 or a nucleotide sequence complementary to SEQ ID NO: 2, provided said functional portion has a nucleotide sequence that is not present in AAV2 (SEQ ID NO: 3) or in AAV3A (SEQ ID NO: 4).

16. The AAV plasmid of claim 15, which is an AAV vector plasmid.

17. The AAV plasmid of claim 15, which is an AAV helper plasmid.

18. A helper cell containing the functional portion of the AAV plasmid of claim 17.

19. The helper cell of claim 18, wherein said functional portion of the nucleotide sequence of SEQ ID NO: 2 encodes a polypeptide selected from the group consisting of an AAV6 viral capsid protein and an AAV6 rep protein.

20. An AAV viral vector, comprising at least a peptide portion of an AAV6 polypeptide, provided said portion is not a portion of an AAV2 polypeptide or an AAV3A polypeptide.

21. The AAV viral vector of claim 20, wherein said polypeptide is an AAV6 capsid protein.

22. A cell containing the AAV viral vector of claim 20.

23. A nucleotide sequence, comprising at least nine unique contiguous nucleotides of SEQ ID NO: 2 or of a sequence complementary to SEQ ID NO: 2.

24. The nucleotide sequence of claim 23, which does not hybridize to a nucleic acid molecule of AAV3B.

25. A method of introducing a heterologous nucleic acid sequence into a mammalian cell, comprising contacting the mammalian cell with an AAV viral vector, comprising an AAV6 vector genome containing at least an unique portion of the nucleotide sequence of SEQ ID NO:2 and containing the heterologous nucleic acid sequence or an AAV viral vector comprising a heterologous nucleic acid and comprising a functional portion of an unique AAV6 polypeptide, under conditions which allow transduction of said mammalian cell, thereby introducing a vector genome containing a heterologous nucleic acid sequence into said mammalian cell.

26. The method of claim 25, wherein said AAV viral vector contains at least a portion of an AAV6 viral capsid protein.

27. The method of claim 25, wherein said heterologous nucleic acid sequence encodes an RNA molecule.

28. The method of claim 25, wherein said heterologous nucleic acid sequence encodes a polypeptide.

29. The method of claim 25, wherein said contacting is performed in vivo.

30. The method of claim 25, wherein said contacting is performed ex vivo.

31. The method of claim 25, wherein said contacting is performed in vitro.

32. The method of claim 25, wherein said mammalian cell is selected from the group consisting of a liver cell, a lung cell, a muscle cell, a fibroblast, a bone marrow cell, an ovary cell, a kidney cell, a brain cell and a tumor cell.

* * * * *

UNITED STATES PATENT AND TRADEMARK OFFICE
CERTIFICATE OF CORRECTION

PATENT NO. : 6,156,303
DATED : December 5, 2000
INVENTOR(S) : Russell, David W. et al.

It is certified that error appears in the above-identified patent and that said Letters Patent is hereby corrected as shown below:

Column 1,
Line 2, please delete "PO1 HL53750" and replace with -- KO8 HL03100 --.

Signed and Sealed this

Eighteenth Day of January, 2005

JON W. DUDAS
*Director of the United States Patent and Trademark Office*

UNITED STATES PATENT AND TRADEMARK OFFICE
CERTIFICATE OF CORRECTION

PATENT NO. : 6,156,303
DATED : December 5, 2000
INVENTOR(S) : Russell, David W. et al.

It is certified that error appears in the above-identified patent and that said Letters Patent is hereby corrected as shown below:

Column 1,
Line 6, after "K08 HL03100" and before "awarded" please insert -- and PO1 HL53750 --.

Signed and Sealed this

Twentieth Day of September, 2005

JON W. DUDAS
*Director of the United States Patent and Trademark Office*

SEQUENCE LISTING

<160> NUMBER OF SEQ ID NOS: 11

<210> SEQ ID NO 1
<211> LENGTH: 4722
<212> TYPE: DNA
<213> ORGANISM: adeno-associated virus 3B

<400> SEQUENCE: 1

| | | | | | | |
|---|---|---|---|---|---|---|
| tggccactcc | ctctatgcgc | actcgctcgc | tcggtggggc | ctggcgacca | aaggtcgcca | 60 |
| gacggacgtg | ctttgcacgt | ccggccccac | cgagcgagcg | agtgcgcata | gagggagtgg | 120 |
| ccaactccat | cactagaggt | atggcagtga | cgtaacgcga | agcgcgcgaa | gcgagaccac | 180 |
| gcctaccagc | tgcgtcagca | gtcaggtgac | ccttttgcga | cagtttgcga | caccacgtgg | 240 |
| ccgctgaggg | tatatattct | cgagtgagcg | aaccaggagc | tccatttttga | ccgcgaaatt | 300 |
| tgaacgagca | gcagccatgc | cggggttcta | cgagattgtc | ctgaaggtcc | cgagtgacct | 360 |
| ggacgagcac | ctgccgggca | tttctaactc | gtttgttaac | tgggtggccg | agaaggaatg | 420 |
| ggagctgccg | ccggattctg | acatggatcc | gaatctgatt | gagcaggcac | ccctgaccgt | 480 |
| ggccgaaaag | cttcagcgcg | agttcctggt | ggagtggcgc | cgcgtgagta | aggcccccgga | 540 |
| ggccctcttt | tttgtccagt | tcgaaaaggg | ggagacctac | ttccacctgc | acgtgctgat | 600 |
| tgagaccatc | ggggtcaaat | ccatggtggt | cggccgctac | gtgagccaga | ttaaagagaa | 660 |
| gctggtgacc | cgcatctacc | gcggggtcga | gccgcagctt | ccgaactggt | tcgcggtgac | 720 |
| caaaacgcga | aatggcgccg | ggggcgggaa | caaggtggtg | gacgactgct | acatccccaa | 780 |
| ctacctgctc | cccaagaccc | agcccgagct | ccagtgggcg | tggactaaca | tggaccagta | 840 |
| tttaagcgcc | tgtttgaatc | tcgcggagcg | taaacggctg | gtggcgcagc | atctgacgca | 900 |
| cgtgtcgcag | acgcaggagc | agaacaaaga | gaatcagaac | cccaattctg | acgcgccggt | 960 |
| catcaggtca | aaaacctcag | ccaggtacat | ggagctggtc | gggtggctgg | tggaccgcgg | 1020 |
| gatcacgtca | gaaaagcaat | ggattcagga | ggaccaggcc | tcgtacatct | ccttcaacgc | 1080 |
| cgcctccaac | tcgcggtccc | agatcaaggc | cgcgctggac | aatgcctcca | gatcatgag | 1140 |
| cctgacaaag | acggctccgg | actacctggt | gggcagcaac | ccgccggagg | acattaccaa | 1200 |
| aaatcggatc | taccaaatcc | tggagctgaa | cgggtacgat | ccgcagtacg | cggcctccgt | 1260 |
| cttcctgggc | tggcgcaaa | agaagttcgg | gaagaggaac | accatctggc | tctttgggcc | 1320 |
| ggccacgacg | ggtaaaacca | acatcgcgga | agccatcgcc | cacgccgtgc | ccttctacgg | 1380 |
| ctgcgtaaac | tggaccaatg | agaactttcc | cttcaacgat | tgcgtcgaca | agatggtgat | 1440 |
| ctggtgggag | gagggcaaga | tgacggccaa | ggtcgtggag | agcgccaagg | ccattctggg | 1500 |
| cggaagcaag | gtgcgcgtgg | accaaaaagtg | caagtcatcg | gcccagatcg | aacccactcc | 1560 |
| cgtgatcgtc | acctccaaca | ccaacatgtg | cgccgtgatt | gacgggaaca | gcaccacctt | 1620 |
| cgagcatcag | cagccgctgc | aggaccggat | gtttaaattt | gaacttaccc | gccgtttgga | 1680 |
| ccatgacttt | gggaaggtca | ccaaacagga | agtaaaggac | ttttttccggt | gggcttccga | 1740 |
| tcacgtgact | gacgtggctc | atgagttcta | cgtcagaaag | ggtggagcta | agaaacgccc | 1800 |
| cgcctccaat | gacgcggatg | taagcgagcc | aaaaacggcag | tgcacgtcac | ttgcgcagcc | 1860 |
| gacaacgtca | gacgcggaag | caccggcgga | ctacgcggac | aggtaccaaa | acaaatgttc | 1920 |
| tcgtcacgtg | ggcatgaatc | tgatgctttt | tccctgtaaa | acatgcgaga | gatgaatca | 1980 |
| aatttccaat | gtctgtttta | cgcatggtca | aagagactgt | ggggaatgct | tccctggaat | 2040 |

-continued

```
gtcagaatct caacccgttt ctgtcgtcaa aaagaagact tatcagaaac tgtgtccaat      2100
tcatcatatc ctgggaaggg cacccgagat tgcctgttcg gcctgcgatt tggccaatgt      2160
ggacttggat gactgtgttt ctgagcaata aatgacttaa accaggtatg gctgctgacg      2220
gttatcttcc agattggctc gaggacaacc tttctgaagg cattcgtgag tggtgggctc      2280
tgaaacctgg agtccctcaa cccaaagcga accaacaaca ccaggacaac cgtcggggtc      2340
ttgtgcttcc gggttacaaa tacctcggac ccggtaacgg actcgacaaa ggagagccgg      2400
tcaacgaggc ggacgcggca gccctcgaac acgacaaagc ttacgaccag cagctcaagg      2460
ccggtgacaa cccgtacctc aagtacaacc acgccgacgc cgagtttcag gagcgtcttc      2520
aagaagatac gtcttttggg ggcaaccttg gcagagcagt cttccaggcc aaaaagagga      2580
tccttgagcc tcttggtctg gttgaggaag cagctaaaac ggctcctgga agaagaggc       2640 ctgtagatca gtctcctcag gaaccggact catcatctgg tgttggcaaa tcgggcaaac      2700
agcctgccag aaaaagacta aatttcggtc agactggcga ctcagagtca gtcccagacc      2760
ctcaacctct cggagaacca ccagcagccc ccacaagttt gggatctaat acaatggctt      2820
caggcggtgg cgcaccaatg gcagacaata cgagggtgc cgatggagtg ggtaattcct       2880
caggaaattg gcattgcgat tcccaatggc tgggcgacag agtcatcacc accagcacca      2940
gaacctgggc cctgcccact tacaacaacc atctctacaa gcaaatctcc agccaatcag      3000
gagcttcaaa cgacaaccac tactttggct acagcacccc ttgggggtat tttgacttta     3060
acagattcca ctgccacttc tcaccacgtg actggcagcg actcattaac aacaactggg      3120
gattccggcc caagaaactc agcttcaagc tcttcaacat ccaagttaaa gaggtcacgc      3180
agaacgatgg cacgacgact attgccaata accttaccag cacggttcaa gtgtttacgg      3240
actcggagta tcagctcccg tacgtgctcg ggtcggcgca ccaaggctgt ctcccgccgt      3300
ttccagcgga cgtcttcatg gtccctcagt atggatacct caccctgaac aacggaagtc      3360
aagcggtggg acgctcatcc ttttactgcc tggagtactt cccttcgcag atgctaagga      3420
ctggaaataa cttccaattc agctatacct tcgaggatgt acctttttcac agcagctacg      3480 ctcacagcca gagtttggat cgcttgatga atcctcttat tgatcagtat ctgtactacc      3540
tgaacagaac gcaaggaaca acctctggaa caaccaacca atcacggctg cttttttagcc     3600 aggctgggcc tcagtctatg tcttttgcagg ccagaaattg gctacctggg ccctgctacc     3660
ggcaacagag actttcaaag actgctaacg acaacaacaa cagtaacttt ccttggacag      3720
cggccagcaa atatcatctc aatggccgcg actcgctggt gaatccagga ccagctatgg      3780
ccagtcacaa ggacgatgaa gaaaaatttt tccctatgca cggcaatcta atatttggca      3840
aagaagggac aacggcaagt aacgcagaat tagataatgt aatgattacg gatgaagaag      3900
agattcgtac caccaatcct gtggcaacag agcagtatgg aactgtggca ataacttgc       3960 agagctcaaa tacagctccc acgactagaa ctgtcaatga tcagggggcc ttacctggca      4020
tggtgtggca agatcgtgac gtgtaccttc aaggacctat ctgggcaaag attcctcaca      4080
cggatggaca ctttcatcct tctcctctga tgggaggctt tggactgaaa catccgcctc      4140
ctcaaatcat gatcaaaaat actccggtac cggcaaatcc tccgacgact ttcagcccgg      4200
ccaagtttgc ttcatttatc actcagtact ccactggaca ggtcagcgtg gaaattgagt      4260
gggagctaca gaaagaaaac agcaaacgtt ggaatccaga gattcagtac acttccaact      4320
acaacaagtc tgttaatgtg gactttactg tagacactaa tggtgtttat agtgaacctc      4380
```

-continued

```
gccctattgg aacccggtat ctcacacgaa acttgtaatc ctggttaatc aataaaccgt    4440
ttaattcgtt tcagttgaac tttggctctt gtgcacttct tatcttatct tgtttccatg    4500
gctactgcgt agataagcag cggcctgcgg cgcttgcgct tcgcggttta caactgctgg    4560
ttaatattta actctcgcca tacctctagt gatggagttg gccactccct ctatgcgcac    4620
tcgctcgctc ggtggggccg gacgtgcaaa gcacgtccgt ctggcgacct ttggtcgcca    4680
ggccccaccg agcgagcgag tgcgcataga gggagtggcc aa                      4722

<210> SEQ ID NO 2
<211> LENGTH: 4683
<212> TYPE: DNA
<213> ORGANISM: adeno-associated virus 6

<400> SEQUENCE: 2
ttggccactc cctctctgcg cgctcgctcg ctcactgagg ccgggcgacc aaaggtcgcc      60
cgacgcccgg gctttgcccg gcggcctcca gtgagcgagc gagcgcgcag agagggagtg    120
gccaactcca tcactagggg ttcctggagg ggtggagtcg tgacgtgaat tacgtcatag    180
ggttagggag gtcctgtatt agaggtcacg tgagtgtttt gcgacatttt gcgacaccat    240
gtggtcacgc tgggtattta agcccgagtg agcacgcagg gtctccattt tgaagcggga    300
ggtttgaacg cgcagcgcca tgccgggggtt ttacgagatt gtgattaagg tccccagcga    360
ccttgacgag catctgcccg gcatttctga cagctttgtg aactgggtgg ccgagaagga    420
atgggagttg ccgccagatt ctgacatgga tctgaatctg attgagcagg cacccctgac    480
cgtggccgag aagctgcagc gcgacttcct ggtccagtgg cgccgcgtga gtaaggcccc    540
ggaggccctc ttctttgttc agttcgagaa gggcgagtcc tacttccacc tccatattct    600
ggtggagacc acgggggtca atccatggt gctgggccgc ttcctgagtc agattaggga    660
caagctggtg cagaccatct accgcgggat cgagccgacc ctgcccaact ggttcgcggt    720
gaccaagacg cgtaatggcg ccggaggggg gaacaaggtg gtggacgagt gctacatccc    780
caactacctc ctgcccaaga ctcagcccga gctgcagtgg gcgtggacta acatggagga    840
gtatataagc gcgtgtttaa acctggccga gcgcaaacgg ctcgtggcgc acgacctgac    900
ccacgtcagc cagacccagg agcagaacaa ggagaatctg aacccaatt ctgacgcgcc    960 tgtcatccgg tcaaaaacct ccgcacgcta catggagctg gtcgggtggc tggtggaccg   1020
gggcatcacc tccgagaagc agtggatcca ggaggaccag gcctcgtaca tctccttcaa   1080
cgccgcctcc aactcgcggt cccagatcaa ggccgctctg acaatgccg gcaagatcat   1140 ggcgctgacc aaatccgcgc ccgactacct ggtaggcccc gctccgcccg ccgacattaa   1200
aaccaaccgc atttaccgca tcctggagct gaacggctac gaccctgcct acgccggctc   1260
cgtcttcctc ggctgggccc agaaaaggtt cggaaaacgc aacaccatct ggctgttggg   1320
gccggccacc acgggcaaga ccaacatcgc ggaagccatc gcccacgccg tgcccttcta   1380
cggctgcgtc aactgaccca atgagaactt tcccttcaac gattgcgtcg acaagatggt   1440
gatctggtgg gaggagggca agatgacggc caaggtcgtg gagtccgcca aggccattct   1500
cggcggcagc aaggtcgcgc tggaccaaaa gtgcaagtcg tccgcccaga tcgatcccac   1560
ccccgtgatc gtcacctcca acaccaacat gtgcgccgtg attgacggga acagcaccac   1620
cttcgagcac cagcagccgt tgcaggacccg gatgttcaaa tttgaactca cccgccgtct   1680
ggagcatgac tttggcaagg tgacaaagca ggaagtcaaa gagttcttcc gctgggcgca   1740
ggatcacgtg accgaggtgg cgcatgagtt ctacgtcaga aagggtggag ccaacaagag   1800
```

-continued

```
acccgccccc gatgacgcgg ataaaagcga gcccaagcgg gcctgcccct cagtcgcgga    1860
tccatcgacg tcagacgcgg aaggagctcc ggtggacttt gccgacaggt accaaaacaa    1920
atgttctcgt cacgcgggca tgcttcagat gctgtttccc tgcaaaacat gcgagagaat    1980
gaatcagaat ttcaacattt gcttcacgca cgggaccaga gactgttcag aatgtttccc    2040
cggcgtgtca gaatctcaac cggtcgtcag aaagaggacg tatcggaaac tctgtgccat    2100
tcatcatctg ctggggcggg ctcccgagat tgcttgctcg gcctgcgatc tggtcaacgt    2160
ggatctggat gactgtgttt ctgagcaata aatgacttaa accaggtatg gctgccgatg    2220
gttatcttcc agattggctc gaggacaacc tctctgaggg cattgcgcag tggtgggact    2280
tgaaacctgg agcccgaaa cccaaagcca accagcaaaa gcaggacgac ggccggggtc    2340
tggtgcttcc tggctacaag tacctcggac ccttcaacgg actcgacaag ggggagcccg    2400
tcaacgcggc ggatgcagcg gccctcgagc acgacaaggc ctacgaccag cagctcaaag    2460
cgggtgacaa tccgtacctg cggtataacc acgccgacgc cgagtttcag gagcgtctgc    2520
aagaagatac gtcttttggg ggcaacctcg ggcgagcagt cttccaggcc aagaagaggg    2580
ttctcgaacc ttttggtctg gttgaggaag gtgctaagac ggctcctgga agaaacgtc    2640 cggtagagca gtcgccacaa gagccagact cctcctcggg cattggcaag acaggccagc    2700
agcccgctaa aaagagactc aattttggtc agactggcga ctcagagtca gtccccgacc    2760
cacaacctct cggagaacct ccagcaaccc ccgctgctgt gggacctact acaatggctt    2820
caggcggtgg cgcaccaatg gcagacaata acgaaggcgc cgacggagtg ggtaatgcct    2880
caggaaattg gcattgcgat tccacatggc tgggcgacag agtcatcacc accagcaccc    2940
gaacatgggc cttgcccacc tataacaacc acctctacaa gcaaatctcc agtgcttcaa    3000 cggggggccag caacgacaac cactacttcg gctacagcac ccctggggg tattttgatt    3060 tcaacagatt ccactgccat ttctcaccac gtgactggca gcgactcatc aacaacaatt    3120
ggggattccg gcccaagaga ctcaacttca agctcttcaa catccaagtc aaggaggtca    3180
cgacgaatga tggcgtcacg accatcgcta ataaccttac cagcacggtt caagtcttct    3240
cggactcgga gtaccagttg ccgtacgtcc tcggctctgc gcaccagggc tgcctccctc    3300
cgttcccggc ggacgtgttc atgattccgc agtacggcta cctaacgctc aacaatggca    3360
gccaggcagt gggacggtca tccttttact gcctggaata tttcccatcg cagatgctga    3420
gaacgggcaa taactttacc ttcagctaca cctttcgagga cgtgccttc cacagcagct    3480 acgcgcacag ccagagcctg gaccggctga tgaatcctct catcgaccag tacctgtatt    3540
acctgaacag aactcagaat cagtccggaa gtgcccaaaa caaggacttg ctgtttagcc    3600 ggggggtctcc agctggcatg tctgttcagc ccaaaaactg gctacctgga ccctgttacc    3660
ggcagcagcg cgtttctaaa acaaaaacag acaacaacaa cagcaacttt acctggactg    3720
gtgcttcaaa atataaccct aatgggcgtg aatctataat caaccctggc actgctatgg    3780
cctcacacaa agacgacaaa gacaagttct ttcccatgag cggtgtcatg attttttggaa    3840 aggagagcgc cggagcttca aacactgcat tggacaatgt catgatcaca gacgaagagg    3900
aaatcaaagc cactaacccc gtggccaccg aaagatttgg gactgtggca gtcaatctcc    3960
agagcagcag cacagaccct gcgaccggag atgtgcatgt tatgggagcc ttacctggaa    4020
tggtgtggca agacagagac gtataccctg cagggtccta tttgggccaaa attcctcaca    4080 cggatggaca ctttcacccg tctcctctca tgggcggctt tggacttaag cacccgcctc    4140
```

-continued

| | |
|---|---|
| ctcagatcct catcaaaaac acgcctgttc ctgcgaatcc tccggcagag ttttcggcta | 4200 |
| caaagtttgc ttcattcatc acccagtatt ccacaggaca agtgagcgtg gagattgaat | 4260 |
| gggagctgca gaaagaaaac agcaaacgct ggaatcccga agtgcagtat acatctaact | 4320 |
| atgcaaaatc tgccaacgtt gatttcactg tggacaacaa tggactttat actgagcctc | 4380 |
| gccccattgg cacccgttac ctcacccgtc cctgtaatt gtgtgttaat caataaaccg | 4440 |
| gttaattcgt gtcagttgaa ctttggtctc atgtcgttat tatcttatct ggtcaccata | 4500 |
| gcaaccggtt acacattaac tgcttagttg cgcttcgcga ataccctag tgatggagtt | 4560 |
| gcccactccc tctatgcgcg ctcgctcgct cggtggggcc ggcagagcag agctctgccg | 4620 |
| tctgcggacc tttggtccgc aggccccacc gagcgagcga gcgcgcatag agggagtggg | 4680 |
| caa | 4683 |

<210> SEQ ID NO 3
<211> LENGTH: 4679
<212> TYPE: DNA
<213> ORGANISM: adeno-associated virus 2

<400> SEQUENCE: 3

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctggagg ggtggagtcg tgacgtgaat tacgtcatag | 180 |
| ggttagggag gtcctgtatt agaggtcacg tgagtgtttt gcgacatttt gcgacaccat | 240 |
| gtggtcacgc tgggtattta gcccgagtg agcacgcagg gtctccattt tgaagcggga | 300 |
| ggtttgaacg cgcagccgcc atgccggggt tttacgagat tgtgattaag gtccccagcg | 360 |
| accttgacgg gcatctgccc ggcatttctg acagctttgt gaactgggtg gccgagaagg | 420 |
| aatgggagtt gccgccagat tctgacatgg atctgaatct gattgagcag caccccctga | 480 |
| ccgtggccga aagctgcag cgcgactttc tgacggaatg gcgccgtgtg agtaaggccc | 540 |
| cggaggcccct tttctttgtg caatttgaga agggagagag ctacttccac atgcacgtgc | 600 |
| tcgtggaaac caccggggtg aaatccatgg ttttgggacg tttcctgagt cagattcgcg | 660 |
| aaaaactgat tcagagaatt taccgcggga tcgagccgac tttgccaaac tggttcgcgg | 720 |
| tcacaaagac cagaaatggc gccggaggcg ggaacaaggt ggtggatgag tgctacatcc | 780 |
| ccaattactt gctccccaaa acccagcctg agctccagtg ggcgtggact aatatggaac | 840 |
| agtatttaag cgcctgtttg aatctcacgg agcgtaaacg gttggtggcg cagcatctga | 900 |
| cgcacgtgtc gcagacgcag gagcagaaca agagaatca gaatcccaat tctgatgcgc | 960 |
| cggtgatcag atcaaaaact tcagccaggt acatggagct ggtcgggtgg ctcgtggaca | 1020 |
| agggattac ctcggagaag cagtggatcc aggaggacca ggcctcatac atctccttca | 1080 |
| atgcggcctc caactcgcgg tcccaaatca aggctgcctt ggacaatgcg ggaaagatta | 1140 |
| tgagcctgac taaaaccgcc cccgactacc tggtgggcca gcagcccgtg gaggacattt | 1200 |
| ccagcaatcg gatttataaa attttggaac taaacgggta cgatcccaa tatgcggctt | 1260 |
| ccgtctttct gggatgggcc acgaaaaagt tcggcaagag gaacaccatc tggctgtttg | 1320 |
| ggcctgcaac taccgggaag accaacatcg cggaggccat agcccacact gtgcccttct | 1380 |
| acgggtgcgt aaactggacc aatgagaact ttccttcaa cgactgtgtc gacaagatgg | 1440 |
| tgatctggtg ggaggagggg aagatgaccg ccaaggtcgt ggagtcggcc aaagccattc | 1500 |
| tcggaggaag caaggtgcgc gtggaccaga aatgcaagtc ctcggcccag atagacccga | 1560 |

-continued

```
ctcccgtgat cgtcacctcc aacaccaaca tgtgcgccgt gattgacggg aactcaacga    1620
ccttcgaaca ccagcagccg ttgcaagacc ggatgttcaa atttgaactc acccgccgtc    1680
tggatcatga ctttgggaag gtcaccaagc aggaagtcaa agacttttc cggtgggcaa     1740 aggatcacgt ggttgaggtg gagcatgaat tctacgtcaa aaagggtgga gccaagaaaa    1800
gacccgcccc cagtgacgca gatataagtg agcccaaacg ggtgcgcgag tcagttgcgc    1860
agccatcgac gtcagacgcg gaagcttcga tcaactacgc agacaggtac caaaacaaat    1920
gttctcgtca cgtgggcatg aatctgatgc tgtttccctg cagacaatgc gagagaatga    1980
atcagaattc aaatatctgc ttcactcacg gacagaaaga ctgtttagag tgctttcccg    2040
tgtcagaatc tcaacccgtt tctgtcgtca aaaaggcgta tcagaaactg tgctacattc    2100
atcatatcat gggaaaggtg ccagacgctt gcactgcctg cgatctggtc aatgtggatt    2160
tggatgactg catctttgaa caataaatga tttaaatcag gtatggctgc cgatggttat    2220
cttccagatt ggctcgagga cactctctct gaaggaataa gacagtggtg gaagctcaaa    2280
cctggcccac caccaccaaa gcccgcagag cggcataagg acgacagcag gggtcttgtg    2340
cttcctgggt acaagtacct cggacccttc aacggactcg acaagggaga gccggtcaac    2400
gaggcagacg ccgcggccct cgagcacgac aaagcctacg accggcagct cgacagcgga    2460
gacaacccgt acctcaagta caaccacgcc gacgcggagt tcaggagcg ccttaaagaa      2520 gatacgtctt tgggggcaa cctcggacga gcagtcttcc aggcgaaaaa gagggttctt      2580
gaacctctgg gcctggttga ggaacctgtt aagacggctc cgggaaaaaa gaggccggta    2640
gagcactctc ctgtggagcc agactcctcc tcgggaaccg gaaaggcggg ccagcagcct    2700
gcaagaaaaa gattgaattt tggtcagact ggagacgcag actcagtacc tgacccccag    2760
cctctcggac agccaccagc agcccctct ggtctgggaa ctaatacgat ggctacaggc      2820
agtggcgcac caatggcaga caataacgag ggcgccgacg gagtgggtaa ttcctccgga    2880
aattggcatt gcgattccac atggatgggc gacagagtca tcaccaccag cacccgaacc    2940
tgggccctgc ccacctacaa caaccacctc tacaaacaaa tttccagcca atcaggagcc    3000
tcgaacgaca atcactactt tggctacagc accccttggg ggtatttga cttcaacaga    3060 ttccactgcc acttttcacc acgtgactgg caaagactca tcaacaacaa ctggggattc    3120
cgacccaaga gactcaactt caagctcttt aacattcaag tcaaagaggt cacgcagaat    3180
gacggtacga cgacgattgc caataacctt accagcacgg ttcaggtgtt tactgactcg    3240
gagtaccagc tcccgtacgt cctcggctcg gcgcatcaag gatgcctccc gccgttccca    3300
gcagacgtct tcatggtgcc acagtatgga tacctcaccc tgaacaacgg gagtcaggca    3360
gtaggacgct cttcattta ctgcctggag tactttcctt ctcagatgct gcgtaccgga    3420
aacaacttta ccttcagcta cacttttgag gacgttcctt tccacagcag ctacgctcac    3480
agccagagtc tggaccgtct catgaatcct ctcatcgacc agtacctgta ttacttgagc    3540
agaacaaaca ctccaagtgg aaccaccacg cagtcaaggc ttcagttttc tcaggccgga    3600
gcgagtgaca ttcgggacca gtctaggaac tggcttcctg gaccctgtta ccgccagcag    3660
cgagtatcaa agacatctgc ggataacaac aacagtgaat actcgtggac tggagctacc    3720
aagtaccacc tcaatggcag agactctctg gtgaatccgg gccggccat ggcaagccac     3780 aaggacgatg aagaaaagtt ttttcctcag agcggggttc tcatctttgg gaagcaaggc    3840
tcagagaaaa caaatgtgga cattgaaaag gtcatgatta cagacgaaga ggaaatcagg    3900
```

-continued

```
acaaccaatc ccgtggctac ggagcagtat ggttctgtat ctaccaacct ccagagaggc    3960
aacagacaag cagctaccgc agatgtcaac acacaaggcg ttcttccagg catggtctgg    4020
caggacagag atgtgtacct tcaggggccc atctgggcaa agattccaca cacggacgga    4080
cattttcacc cctctcccct catgggtgga ttcggactta acaccctcc tccacagatt     4140 ctcatcaaga acccccggt acctgcgaat ccttcgacca ccttcagtgc ggcaaagttt     4200
gcttccttca tcacacagta ctccacggga caggtcagcg tggagatcga gtgggagctg    4260
cagaaggaaa acagcaaacg ctggaatccc gaaattcagt acacttccaa ctacaacaag    4320
tctgttaatg tggactttac tgtggacact aatggcgtgt attcagagcc tcgccccatt    4380
ggcaccagat acctgactcg taatctgtaa ttgcttgtta atcaataaac cgtttaattc    4440
gtttcagttg aactttggtc tctgcgtatt tctttcttat ctagtttcca tggctacgta    4500
gataagtagc atggcgggtt aatcattaac tacaaggaac ccctagtgat ggagttggcc    4560
actccctctc tgcgcgctcg ctcgctcact gaggccgggc gaccaaaggt cgcccgacgc    4620
ccgggctttg cccggcggc ctcagtgagc gagcgagcgc gcagagaggg agtggccaa     4679
```

<210> SEQ ID NO 4
<211> LENGTH: 735
<212> TYPE: PRT
<213> ORGANISM: adeno-associated virus 2

<400> SEQUENCE: 4

```
Met Ala Ala Asp Gly Tyr Leu Pro Asp Trp Leu Glu Asp Thr Leu Ser
 1               5                  10                  15

Glu Gly Ile Arg Gln Trp Trp Lys Leu Lys Pro Gly Pro Pro Pro
             20                  25                  30

Lys Pro Ala Glu Arg His Lys Asp Asp Ser Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240
```

```
Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
        260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
```

-continued

```
                660                 665                 670
Tyr Ser Thr Gly Gln Val Ser Glu Ile Glu Trp Glu Leu Gln Lys
            675                 680                 685
Glu Asn Ser Lys Arg Trp Asn Pro Glu Ile Gln Tyr Thr Ser Asn Tyr
            690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 5
<211> LENGTH: 736
<212> TYPE: PRT
<213> ORGANISM: adeno-associated virus 3A

<400> SEQUENCE: 5

Met Ala Ala Asp Gly Tyr Leu Pro Asp Trp Leu Glu Asp Asn Leu Ser
  1               5                  10                  15
Glu Gly Ile Arg Glu Trp Trp Ala Leu Lys Pro Gly Val Pro Gln Pro
                 20                  25                  30
Lys Ala Asn Gln Gln His Gln Asp Asn Arg Arg Gly Leu Val Leu Pro
             35                  40                  45
Gly Tyr Lys Tyr Leu Gly Pro Gly Asn Gly Leu Asp Lys Gly Glu Pro
         50                  55                  60
Val Asn Glu Ala Asp Ala Ala Leu Glu His Asp Lys Ala Tyr Asp
 65                  70                  75                  80
Gln Gln Leu Lys Ala Gly Asp Asn Pro Tyr Leu Lys Tyr Asn His Ala
                 85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Ile Leu Glu Pro
            115                 120                 125
Leu Gly Leu Val Glu Glu Ala Ala Lys Thr Ala Pro Gly Lys Lys Gly
        130                 135                 140
Ala Val Asp Gln Ser Pro Gln Glu Pro Asp Ser Ser Ser Gly Val Gly
145                 150                 155                 160
Lys Ser Gly Lys Gln Pro Ala Arg Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Ala Pro Thr Ser Leu Gly Ser Asn Thr Met Ala Ser Gly Gly Gly
        195                 200                 205
Ala Pro Met Ala Asp Asn Asn Glu Gly Ala Asp Gly Val Gly Asn Ser
210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
290                 295                 300
```

-continued

```
Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
            485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
            530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
            565                 570                 575

Tyr Gly Thr Val Ala Asn Asn Leu Gln Ser Ser Asn Thr Ala Pro Thr
            580                 585                 590

Thr Gly Thr Val Asn His Gln Gly Ala Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Gln Ile Met Ile Lys Asn Thr Pro Val Pro Ala
            645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
```

725                 730                 735

<210> SEQ ID NO 6
<211> LENGTH: 736
<212> TYPE: PRT
<213> ORGANISM: adeno-associated virus 3B

<400> SEQUENCE: 6

Met Ala Ala Asp Gly Tyr Leu Pro Asp Trp Leu Glu Asp Asn Leu Ser
 1               5                  10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
         370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 7
<211> LENGTH: 736
<212> TYPE: PRT
<213> ORGANISM: adeno-associated virus 6

<400> SEQUENCE: 7

Met Ala Ala Asp Gly Tyr Leu Pro Asp Trp Leu Glu Asp Asn Leu Ser
 1               5                  10                  15

-continued

```
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
         35                  40                  45
Gly Tyr Lys Tyr Leu Gly Pro Phe Asn Gly Leu Asp Lys Gly Glu Pro
     50                  55                  60
Val Asn Ala Ala Asp Ala Ala Leu Glu His Asp Lys Ala Tyr Asp
 65                  70                  75                  80
Gln Gln Leu Lys Ala Gly Asp Asn Pro Tyr Leu Arg Tyr Asn His Ala
                 85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Phe Gly Leu Val Glu Glu Gly Ala Lys Thr Ala Pro Gly Lys Lys Arg
    130                 135                 140
Pro Val Glu Gln Ser Pro Gln Glu Pro Asp Ser Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Thr Pro Ala Ala Val Gly Pro Thr Thr Met Ala Ser Gly Gly Gly
        195                 200                 205
Ala Pro Met Ala Asp Asn Asn Glu Gly Ala Asp Gly Val Gly Asn Ala
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
            260                 265                 270
Tyr Phe Gly Tyr Ser Thr Pro Trp Gly Tyr Phe Asp Phe Asn Arg Phe
        275                 280                 285
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
        355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Asp Val Pro Phe His Ser Ser Tyr Ala His Ser Gln Ser Leu Asp
            420                 425                 430
```

-continued

```
Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
        450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 8
<211> LENGTH: 621
<212> TYPE: PRT
<213> ORGANISM: adeno-associated virus 2

<400> SEQUENCE: 8

Met Pro Gly Phe Tyr Glu Ile Val Ile Lys Val Pro Ser Asp Leu Asp
  1               5                  10                  15

Gly His Leu Pro Gly Ile Ser Asp Ser Phe Val Asn Trp Val Ala Glu
             20                  25                  30

Lys Glu Trp Glu Leu Pro Pro Asp Ser Asp Met Asp Leu Asn Leu Ile
         35                  40                  45

Glu Gln Ala Pro Leu Thr Val Ala Glu Lys Leu Gln Arg Asp Phe Leu
     50                  55                  60

Thr Glu Trp Arg Arg Val Ser Lys Ala Pro Glu Ala Leu Phe Phe Val
 65                  70                  75                  80
```

-continued

```
Gln Phe Glu Lys Gly Glu Ser Tyr Phe His Met His Val Leu Val Glu
                85                  90                  95
Thr Thr Gly Val Lys Ser Met Val Leu Gly Arg Phe Leu Ser Gln Ile
            100                 105                 110
Arg Glu Lys Leu Ile Gln Arg Ile Tyr Arg Gly Ile Glu Pro Thr Leu
        115                 120                 125
Pro Asn Trp Phe Ala Val Thr Lys Thr Arg Asn Gly Ala Gly Gly Gly
    130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Gln Tyr Leu
                165                 170                 175
Ser Ala Cys Leu Asn Leu Thr Glu Arg Lys Arg Leu Val Ala Gln His
            180                 185                 190
Leu Thr His Val Ser Gln Thr Gln Glu Gln Asn Lys Glu Asn Gln Asn
        195                 200                 205
Pro Asn Ser Asp Ala Pro Val Ile Arg Ser Lys Thr Ser Ala Arg Tyr
    210                 215                 220
Met Glu Leu Val Gly Trp Leu Val Asp Lys Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
            260                 265                 270
Ile Met Ser Leu Thr Lys Thr Ala Pro Asp Tyr Leu Val Gly Gln Gln
        275                 280                 285
Pro Val Glu Asp Ile Ser Ser Asn Arg Ile Tyr Lys Ile Leu Glu Leu
    290                 295                 300
Asn Gly Tyr Asp Pro Gln Tyr Ala Ala Ser Val Phe Leu Gly Trp Ala
305                 310                 315                 320
Thr Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Thr Val Pro
            340                 345                 350
Phe Tyr Gly Cys Val Asn Trp Thr Asn Glu Asn Phe Pro Phe Asn Asp
        355                 360                 365
Cys Val Asp Lys Met Val Ile Trp Trp Glu Glu Gly Lys Met Thr Ala
    370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
        435                 440                 445
Glu Leu Thr Arg Arg Leu Asp His Asp Phe Gly Lys Val Thr Lys Gln
    450                 455                 460
Glu Val Lys Asp Phe Phe Arg Trp Ala Lys Asp His Val Val Glu Val
465                 470                 475                 480
Glu His Glu Phe Tyr Val Lys Lys Gly Gly Ala Lys Lys Arg Pro Ala
                485                 490                 495
```

```
Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
    530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
    610                 615                 620

<210> SEQ ID NO 9
<211> LENGTH: 624
<212> TYPE: PRT
<213> ORGANISM: adeno-associated virus 3A

<400> SEQUENCE: 9

Met Pro Gly Phe Tyr Glu Ile Val Leu Lys Val Pro Ser Asp Leu Asp
  1               5                  10                  15

Glu Arg Leu Pro Gly Ile Ser Asn Ser Phe Val Asn Trp Val Ala Glu
                20                  25                  30

Lys Glu Trp Asp Val Pro Pro Asp Ser Asp Met Asp Pro Asn Leu Ile
            35                  40                  45

Glu Gln Ala Pro Leu Thr Val Ala Glu Lys Leu Gln Arg Glu Phe Leu
        50                  55                  60

Val Glu Trp Arg Arg Val Ser Lys Ala Pro Glu Ala Leu Phe Phe Val
 65                  70                  75                  80

Gln Phe Glu Lys Gly Glu Thr Tyr Phe His Leu His Val Leu Ile Glu
                85                  90                  95

Thr Ile Gly Val Lys Ser Met Val Val Gly Arg Tyr Val Ser Gln Ile
                100                 105                 110

Lys Glu Lys Leu Val Thr Arg Ile Tyr Arg Gly Val Glu Pro Gln Leu
            115                 120                 125

Pro Asn Trp Phe Ala Val Thr Lys Thr Arg Asn Gly Ala Gly Gly Gly
    130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Leu
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255
```

Ser Asn Ser Arg Ser Gln Ile Lys Ala Ala Leu Asp Asn Ala Ser Lys
            260                 265                 270

Ile Met Ser Leu Thr Lys Thr Ala Pro Asp Tyr Leu Val Gly Ser Asn
        275                 280                 285

Pro Pro Glu Asp Ile Thr Lys Asn Arg Ile Tyr Gln Ile Leu Glu Leu
    290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Glu Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Glu Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
                485                 490                 495

Ser Asn Asp Ala Asp Val Ser Glu Pro Lys Arg Glu Cys Thr Ser Leu
            500                 505                 510

Ala Gln Pro Thr Thr Ser Asp Ala Glu Ala Pro Ala Asp Tyr Ala Asp
        515                 520                 525

Arg Tyr Gln Asn Lys Cys Ser Arg His Val Gly Met Asn Leu Met Leu
    530                 535                 540

Phe Pro Cys Lys Thr Cys Glu Arg Met Asn Gln Ile Ser Asn Val Cys
545                 550                 555                 560

Phe Thr His Gly Gln Arg Asp Cys Gly Glu Cys Phe Pro Gly Met Ser
                565                 570                 575

Glu Ser Gln Pro Val Ser Val Val Lys Lys Lys Thr Tyr Gln Lys Leu
            580                 585                 590

Cys Pro Ile His His Ile Leu Gly Arg Ala Pro Glu Ile Ala Cys Ser
        595                 600                 605

Ala Cys Asp Leu Ala Asn Val Asp Leu Asp Asp Cys Val Ser Glu Gln
    610                 615                 620

<210> SEQ ID NO 10
<211> LENGTH: 624
<212> TYPE: PRT
<213> ORGANISM: adeno-associated virus 3B

<400> SEQUENCE: 10

Met Pro Gly Phe Tyr Glu Ile Val Leu Lys Val Pro Ser Asp Leu Asp

-continued

```
  1               5                  10                 15
Glu His Leu Pro Gly Ile Ser Asn Ser Phe Val Asn Trp Val Ala Glu
                20                 25                 30
Lys Glu Trp Glu Leu Pro Pro Asp Ser Asp Met Asp Pro Asn Leu Ile
                35                 40                 45
Glu Gln Ala Pro Leu Thr Val Ala Glu Lys Leu Gln Arg Glu Phe Leu
                50                 55                 60
Val Glu Trp Arg Arg Val Ser Lys Ala Pro Glu Ala Leu Phe Phe Val
 65                 70                 75                 80
Gln Phe Glu Lys Gly Glu Thr Tyr Phe His Leu His Val Leu Ile Glu
                85                 90                 95
Thr Ile Gly Val Lys Ser Met Val Val Gly Arg Tyr Val Ser Gln Ile
               100                105                110
Lys Glu Lys Leu Val Thr Arg Ile Tyr Arg Gly Val Glu Pro Gln Leu
               115                120                125
Pro Asn Trp Phe Ala Val Thr Lys Thr Arg Asn Gly Ala Gly Gly Gly
               130                135                140
Asn Lys Val Val Asp Asp Cys Tyr Ile Pro Asn Tyr Leu Leu Pro Lys
145                150                155                160
Thr Gln Pro Glu Leu Gln Trp Ala Trp Thr Asn Met Asp Gln Tyr Leu
               165                170                175
Ser Ala Cys Leu Asn Leu Ala Glu Arg Lys Arg Leu Val Ala Gln His
               180                185                190
Leu Thr His Val Ser Gln Thr Gln Glu Gln Asn Lys Glu Asn Gln Asn
               195                200                205
Pro Asn Ser Asp Ala Pro Val Ile Arg Ser Lys Thr Ser Ala Arg Tyr
               210                215                220
Met Glu Leu Val Gly Trp Leu Val Asp Arg Gly Ile Thr Ser Glu Lys
225                230                235                240
Gln Trp Ile Gln Glu Asp Gln Ala Ser Tyr Ile Ser Phe Asn Ala Ala
               245                250                255
Ser Asn Ser Arg Ser Gln Ile Lys Ala Ala Leu Asp Asn Ala Ser Lys
               260                265                270
Ile Met Ser Leu Thr Lys Thr Ala Pro Asp Tyr Leu Val Gly Ser Asn
               275                280                285
Pro Pro Glu Asp Ile Thr Lys Asn Arg Ile Tyr Gln Ile Leu Glu Leu
               290                295                300
Asn Gly Tyr Asp Pro Gln Tyr Ala Ala Ser Val Phe Leu Gly Trp Ala
305                310                315                320
Gln Lys Lys Phe Gly Lys Arg Asn Thr Ile Trp Leu Phe Gly Pro Ala
               325                330                335
Thr Thr Gly Lys Thr Asn Ile Ala Glu Ala Ile Ala His Ala Val Pro
               340                345                350
Phe Tyr Gly Cys Val Asn Trp Thr Asn Glu Asn Phe Pro Phe Asn Asp
               355                360                365
Cys Val Asp Lys Met Val Ile Trp Trp Glu Glu Gly Lys Met Thr Ala
               370                375                380
Lys Val Val Glu Ser Ala Lys Ala Ile Leu Gly Gly Ser Lys Val Arg
385                390                395                400
Val Asp Gln Lys Cys Lys Ser Ser Ala Gln Ile Glu Pro Thr Pro Val
               405                410                415
Ile Val Thr Ser Asn Thr Asn Met Cys Ala Val Ile Asp Gly Asn Ser
               420                425                430
```

-continued

```
Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
        450                 455                 460

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
                485                 490                 495

Ser Asn Asp Ala Asp Val Ser Glu Pro Lys Arg Gln Cys Thr Ser Leu
            500                 505                 510

Ala Gln Pro Thr Thr Ser Asp Ala Glu Ala Pro Ala Asp Tyr Ala Asp
        515                 520                 525

Arg Tyr Gln Asn Lys Cys Ser Arg His Val Gly Met Asn Leu Met Leu
    530                 535                 540

Phe Pro Cys Lys Thr Cys Glu Arg Met Asn Gln Ile Ser Asn Val Cys
545                 550                 555                 560

Phe Thr His Gly Gln Arg Asp Cys Gly Glu Cys Phe Pro Gly Met Ser
                565                 570                 575

Glu Ser Gln Pro Val Ser Val Val Lys Lys Lys Thr Tyr Gln Lys Leu
            580                 585                 590

Cys Pro Ile His His Ile Leu Gly Arg Ala Pro Glu Ile Ala Cys Ser
        595                 600                 605

Ala Cys Asp Leu Ala Asn Val Asp Leu Asp Asp Cys Val Ser Glu Gln
    610                 615                 620

<210> SEQ ID NO 11
<211> LENGTH: 623
<212> TYPE: PRT
<213> ORGANISM: adeno-associated virus 6

<400> SEQUENCE: 11

Met Pro Gly Phe Tyr Glu Ile Val Ile Lys Val Pro Ser Asp Leu Asp
1               5                  10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala His Asp
```

-continued

```
                180             185             190
Leu Thr His Val Ser Gln Thr Gln Glu Gln Asn Lys Glu Asn Leu Asn
                195             200             205
Pro Asn Ser Asp Ala Pro Val Ile Arg Ser Lys Thr Ser Ala Arg Tyr
            210             215             220
Met Glu Leu Val Gly Trp Leu Val Asp Arg Gly Ile Thr Ser Glu Lys
225             230             235             240
Gln Trp Ile Gln Glu Asp Gln Ala Ser Tyr Ile Ser Phe Asn Ala Ala
                245             250             255
Ser Asn Ser Arg Ser Gln Ile Lys Ala Ala Leu Asp Asn Ala Gly Lys
            260             265             270
Ile Met Ala Leu Thr Lys Ser Ala Pro Asp Tyr Leu Val Gly Pro Ala
        275             280             285
Pro Pro Ala Asp Ile Lys Thr Asn Arg Ile Tyr Arg Ile Leu Glu Leu
    290             295             300
Asn Gly Tyr Asp Pro Ala Tyr Ala Gly Ser Val Phe Leu Gly Trp Ala
305             310             315             320
Gln Lys Arg Phe Gly Lys Arg Asn Thr Ile Trp Leu Phe Gly Pro Ala
                325             330             335
Thr Thr Gly Lys Thr Asn Ile Ala Glu Ala Ile Ala His Ala Val Pro
            340             345             350
Phe Tyr Gly Cys Val Asn Trp Thr Asn Glu Asn Phe Pro Phe Asn Asp
        355             360             365
Cys Val Asp Lys Met Val Ile Trp Trp Glu Glu Gly Lys Met Thr Ala
    370             375             380
Lys Val Val Glu Ser Ala Lys Ala Ile Leu Gly Gly Ser Lys Val Arg
385             390             395             400
Val Asp Gln Lys Cys Lys Ser Ser Ala Gln Ile Asp Pro Thr Pro Val
                405             410             415
Ile Val Thr Ser Asn Thr Asn Met Cys Ala Val Ile Asp Gly Asn Ser
            420             425             430
Thr Thr Phe Glu His Gln Gln Pro Leu Gln Asp Arg Met Phe Lys Phe
        435             440             445
Glu Leu Thr Arg Arg Leu Glu His Asp Phe Gly Lys Val Thr Lys Gln
    450             455             460
Glu Val Lys Glu Phe Phe Arg Trp Ala Gln Asp His Val Thr Glu Val
465             470             475             480
Ala His Glu Phe Tyr Val Arg Lys Gly Gly Ala Asn Lys Arg Pro Ala
                485             490             495
Pro Asp Asp Ala Asp Lys Ser Glu Pro Lys Arg Ala Cys Pro Ser Val
            500             505             510
Ala Asp Pro Ser Thr Ser Asp Ala Glu Gly Ala Pro Val Asp Phe Ala
        515             520             525
Asp Arg Tyr Gln Asn Lys Cys Ser Arg His Ala Gly Met Leu Gln Met
    530             535             540
Leu Phe Pro Cys Lys Thr Cys Glu Arg Met Asn Gln Asn Phe Asn Ile
545             550             555             560
Cys Phe Thr His Gly Thr Arg Asp Cys Ser Glu Cys Phe Pro Gly Val
                565             570             575
Ser Glu Ser Gln Pro Val Val Arg Lys Arg Thr Tyr Arg Lys Leu Cys
            580             585             590
Ala Ile His His Leu Leu Gly Arg Ala Pro Glu Ile Ala Cys Ser Ala
        595             600             605
```

```
-continued

Cys Asp Leu Val Asn Val Asp Leu Asp Asp Cys Val Ser Glu Gln
    610             615             620
```